US012708321B2

(12) United States Patent
Erdoğan et al.

(10) Patent No.: US 12,708,321 B2
(45) Date of Patent: Aug. 18, 2026

(54) SYSTEM AND METHOD FOR EVALUATING FEEDING MATURATION

(71) Applicant: KUARTISMED MEDIKAL ARAŞ. GELIŞ.DAN.EĞT.SAN. VE TIC. A.Ş., Cankaya-Ankara (TR)

(72) Inventors: Balkar Erdoğan, Ankara (TR); Ahmet Saracoğlu, Ankara (TR); Aylin Tarcan, Ankara (TR); Osman Serdar Gedik, Ankara (TR); Ayşe Nur Ecevit, Ankara (TR); Nur Benli, Ankara (TR); Elyar Ghalichi, Ankara (TR)

(73) Assignee: KUARTISMED MEDIKAL ARAS.GELIS.DAN.EGT.SAN. VE TIC. A.S. (TR)

( * ) Notice: Subject to any disclaimer, the term of this patent is extended or adjusted under 35 U.S.C. 154(b) by 736 days.

(21) Appl. No.: 17/796,721

(22) PCT Filed: Jan. 29, 2021

(86) PCT No.: PCT/EP2021/052214
§ 371 (c)(1),
(2) Date: Aug. 1, 2022

(87) PCT Pub. No.: WO2021/152151
PCT Pub. Date: Aug. 5, 2021

(65) Prior Publication Data

US 2023/0069209 A1 Mar. 2, 2023

(30) Foreign Application Priority Data

Jan. 31, 2020 (GB) ..................................... 2001394

(51) Int. Cl.
*A61B 5/00* (2006.01)
*A61B 5/08* (2006.01)
(Continued)

(52) U.S. Cl.
CPC .......... *A61B 5/4205* (2013.01); *A61B 5/0816* (2013.01); *A61B 5/113* (2013.01);
(Continued)

(58) Field of Classification Search
CPC ..... A61B 5/4205; A61B 5/0816; A61B 5/113; A61B 5/4803; A61B 5/725; A61B 5/7267;
(Continued)

(56) References Cited

U.S. PATENT DOCUMENTS 5,934,925 A 8/1999 Tobler et al.
2007/0219059 A1* 9/2007 Schwartz ............... A61B 5/329 482/8

(Continued)

FOREIGN PATENT DOCUMENTS

KR 20170100932 A 9/2017
WO 2013/138071 A1 9/2013
WO 2019/161277 A1 8/2019

OTHER PUBLICATIONS

Vice et al., Cervical Auscultation of Suckle Feeding in Newborn Infants, 1990, Developmental Medicine and Child Neurology, vol. 32, pp. 760-768 (Year: 1990).*

(Continued)

*Primary Examiner* — Catherine M Voorhees
(74) *Attorney, Agent, or Firm* — Conley Rose, P.C.

(57) ABSTRACT

A method for monitoring feeding maturation in premature babies, the method including measuring an acoustic response from a baby during a selected time period to provide acoustic information; comparing the measured acoustic response against a train data set to determine an indication of a swallow event; and measuring a respiration pattern of the baby during a swallow cycle using a peak and valley model to provide respiration data, where a feeding
(Continued)

maturity of the baby is determinable in dependence on the swallow indication and respiration data.

12 Claims, 26 Drawing Sheets

(51) Int. Cl.
*A61B 5/113* (2006.01)
*A61B 7/00* (2006.01)

(52) U.S. Cl.
CPC .......... *A61B 5/4803* (2013.01); *A61B 5/6833* (2013.01); *A61B 5/725* (2013.01); *A61B 5/7267* (2013.01); *A61B 5/7282* (2013.01); *A61B 7/008* (2013.01); *A61B 2503/045* (2013.01); *A61B 2562/0204* (2013.01); *A61B 2562/0247* (2013.01); *A61B 2562/028* (2013.01); *A61B 2562/225* (2013.01)

(58) Field of Classification Search
CPC ............ A61B 5/7282; A61B 2503/045; A61B 2562/0204; A61B 7/003
See application file for complete search history.

(56) References Cited

U.S. PATENT DOCUMENTS

2012/0276786 A1 11/2012 Al-Ali et al.
2015/0080672 A1* 3/2015 Biswas ................ A61B 5/1135 600/301
2016/0235353 A1* 8/2016 Nakar .................... A61B 7/008
2019/0313915 A1* 10/2019 Tzvieli ...................... G01J 5/12
2021/0113099 A1* 4/2021 Rogers ................. A61B 5/4803

OTHER PUBLICATIONS

Wang et al., Design of wireless multi-parameter monitoring system for oral feeding of premature infants, 2016, Med Biol Eng Comput, vol. 54 pp. 1061-1069 (Year: 2016).*
Wang Yu-Lin et al: "Design of wireless multi-parameter monitoring system for oral feeding of premature infants", Medical and Biological Engineering and Computing, Springer, Heildelberg, DE, vol. 54, No. 7. Oct. 1, 2015, pp. 1061-1069.
Frakking Thuy T. et al: "Acoustic and Perceptual Profiles of Swallowing Sounds in Children: Normative Data for 4-36 Months from a Cross-Sectional Study Cohort", Dysphagia, Springer, Boston, vol. 32, No. 2. Nov. 9, 2016, pp. 261-270.
Frank L. Vice et al: "Cervical Auscultation of Suckle Feeding in Newborn Infants", Developmental Medicine & Child Neurology, vol. 32, No. 9. Sep. 1, 1990, pp. 760-768.
International Search Report and Written Opinion dated Sep. 7, 2021, for Application No. PCT/EP2021/052214.

* cited by examiner

Praat view of two episodes for both "y" and "n" classes.

Two swallow events in a compact form, no initial or final sounds

Two swallow events, the "rsp-y-fds" pattern

Two swallow events, the "y-fds" pattern

*A false positive at the beginning*

*Three examples of the raw data of the digitized respiration signal.*

*Smoothed and normalized respiration signal examples.*

Connector
Enclosure - Top
Connector Electronic
Circuit - PCB
Connector
Enclosure - Bottom
78
82
84
72
94
80

74
Probe
Front-End
Probe Cable

76
Connector
72

100
SSP Connector
Enclosure Top Part
SSP Connector
Enclosure Bottom Part
72

100
SSP Connector
Enclosure Bottom Part
SSP Connector
Enclosure Top Part
72

SYSTEM AND METHOD FOR EVALUATING FEEDING MATURATION

CROSS-REFERENCE TO RELATED APPLICATIONS

This application is a 35 U.S.C. § 371 national stage application of PCT/EP2021/052214 filed Jan. 29, 2021, and entitled "System and Method for Evaluating Feeding Maturation" which claims priority to United Kingdom patent application No. GB 2001394.2 filed Jan. 31, 2020, both of which are hereby incorporated herein by reference in their entirety.

FIELD OF THE DESCRIPTION

This description relates to a system and method for evaluating feeding maturation. In embodiments, the present description relates to a method, system and device for monitoring and/or evaluating feeding maturation in infants that are born prematurely.

BACKGROUND

Most babies who are born after the regular gestation period display developed sucking-swallowing capabilities. However, these capabilities are underdeveloped in babies who are born prematurely. The lack of development of effective feeding in premature babies can lead to eating disorders, accidental deposits of food in the respiratory tract and the lungs, respiratory illnesses related thereto, infections, respiratory arrest and even death. Further, this can also cause infants to quickly become fatigued and thus impact their growth. For this reason, babies are fed with probes fitted in the stomach for the majority of their intensive care observation.

As described in our earlier published application WO-A-2014/081401, currently, in practice, doctors utilize trial-and-error techniques or observational criteria that are, for the most part, subjective, in order to gauge effective and safe feeding. Efforts aimed at more objective assessment techniques have focused on invasive, pressure measurement methods that can be particularly painful for infants. However, such methods are not practical or well-suited for regular monitoring. Numerous methods, most of which include invasive applications, are used to evaluate swallowing function in adults and children.

These include evaluating pharyngo-oesophageal motility through miromanometry, recording motor response potential in pharyngeal and frontal hyomandibular muscles, video fluoroscopic swallow studies and fibre-optic endoscopic evaluation of swallowing. See for example, in Shin, H. S., Lee, C., & Lee, M. (2009), Adaptive threshold method for the peak detection of photoplethysmographic waveform published in *Computers in biology and medicine,* 39(12), 1145-1152.

Video fluoroscopic swallow studies (VFSS) are frequently evaluated using modified barium and are employed to examine the swallowing mechanism and define the pathophysiology of swallowing disorders. See for example, 1) B. Martin-Harris and B. Jones, "The videofluorographic swallowing study," Physical medicine and rehabilitation clinics of North America, vol. 19, no. 4, pp. 769-785, 2008.
2) S. T. Almeida, E. L. Ferlin, M. A. M. Parente, and H. A. Goldani, "Assessment of swallowing sounds by digital cervical auscultation in children," Annals of Otology, Rhinology & Laryngology, vol. 117, no. 4, pp. 253-258, 2008.

In a study carried out on preterm new-borns, published in a paper by A, Smith V, Ringer S, Richardson M J, Wolff P H entitled "Premature infant swallowing: Patterns of tongue-soft palate coordination based upon video fluoroscopy" in Infant Behav Dev 2010 ;33:209-1812, preterm new-borns were evaluated for tongue and soft palate elevation coordination during swallowing using VFSS and mother's milk or formula mixed with barium sulphate. Video footage was recorded during a maximum total radiation exposure time of three minutes. Through this method, tongue movements and the elevation of the soft palate were observed.

Other methods and studies of infant and human swallowing have been conducted and are described in the following papers:

Sitton M, Arvedson J, Visotcky A, Braun N, Kerschner J, Tarima S, Brown D. Fiberoptic endoscopic evaluation of swallowing in children: feeding outcomes related to diagnostic groups and endoscopic findings. Int J Pediatr Otorhinolaryngol. 2011; 75:1024-31;

Geddes D T, Chadwick L M, Kent J C, Garbin C P, Hartmann P E. Ultrasound imaging of infant swallowing during breast-feeding. Dysphagia 2010; 25(3): 183-91;

Takahashi K, Groher M E, Michi K. Methodology for detecting swallowing sounds. Dysphagia. 1994; 9:54-62;

Reynolds E W, Vice F L, Gewolb I H. Cervical accelerometry in preterm infants with and without bronchopulmonary dysplasia. Dev Med Child Neurol. 2003; 45:442-6;

Reynolds E W, Vice F L, Gewolb I H. Variability of swallow-associated sounds in adults and infants. Dysphagia. 2009; 24:13-9; and Barlow S M. Central pattern generation involved in oral and respiratory control for feeding in the term infant. Curr Opin Otolaryngol Head Neck Surg. 2009; 17:187-93.

Furthermore, patent applications have been filed relating to solutions and devices aimed at enabling feeding maturation through the assessment of sucking-swallowing-breathing coordination. See for example US-A-2010/0056961. The described device senses the functions of sucking, swallowing and breathing through different sensors. In summary, the device analyses the succession of occurrence on the timeline of the swallowing and breathing recordings, which are initiated together with the sucking function, and provides a diagnosis based on its assessment of swallowing-breathing coordination. However, there is currently no clinically proven reliable device or method that is viably able to assess feeding maturation in infants through objective measuring.

Similarly, US-A-2010/0145166 discloses an integrated device that assesses a baby's feeding maturation based on the times of occurrence of the sucking, swallowing and breathing events.

A problem arises in identification of a swallowing event. If a false result occurs either as a false positive or a missed actual swallowing event, then the output data and any subsequent decisions can be faulty.

SUMMARY

According to a first aspect of the present description, there is provided a method for monitoring feeding maturation in premature babies, the method comprising; measuring the acoustic response from a baby during a selected time period to provide acoustic information and comparing the measured response against a train data set to determine an indication of a swallow event; measuring the respiration pattern of the baby during the swallow cycle using a peak and valley model to provide respiration information; wherein, in dependence on the provided swallow and respiration data, the feeding maturity of the baby can be determined.

In an embodiment, the step of measuring the acoustic response from a baby during a selected time period comprises extracting features from a received signal and comparing the extracted features against the data set, wherein the extracted features may be classified as swallow or a non-swallow events.

In an embodiment, prior to the step of extracting features, a received signal is framed so as to be considered as stationary.

In an embodiment, the comparison against the set comprises comparing extracted features in a classification process.

In an embodiment, feature extraction is performed using a speech analysis tool.

In an embodiment, the feature extraction comprises labelling identified features as one or more of features selected from the group including:

I. swallow sound
II. final discrete sound
III. respiration sound
IV. other non-swallow sounds such as vowel, pleasure or crying.

In an embodiment, the average time between swallows and the number of maximum rhythmic swallows are calculated to enable determination of feeding maturity.

In an embodiment, training of the data set comprises: receiving audio samples from healthy subjects; framing the received audio samples so as to provide stationary signals; extracting features from the framed samples so as to generate the train data set.

In an embodiment, the peak valley method used to determine respiration data comprises: receiving an input signal indicating respiration; processing the received signal with a low pass filter so as to provide a smoothed respiration signal; and based on the smoothed respiration signal extracting parameters associated with the respiration.

In an embodiment, the parameters include one or more of breath rate, and onset or end of an inspiration or expiration event.

In an embodiment, in dependence on the captured data representing swallow and respiration statistics, the inspiration after swallow count is determined thereby indicating the number of inspiration events occurring just after a swallow event has finished, wherein if it increases, it is determined that feeding maturity decreases.

There is provided a system for monitoring the feeding maturation in a premature baby, the system comprising; a sensor for measuring the acoustic response from a baby during a selected time period to provide acoustic information; a sensor for measuring the respiration pattern of the baby during the swallow cycle; and a processor the processor being arranged and configured to compare the measured acoustic response against a train data set to determine an indication of a swallow event; and being arranged and configured to use a peak and valley model to provide respiration information based on the measured respiration pattern; wherein, in dependence on the provided swallow and respiration data a feeding maturity of the baby can be determined.

In an embodiment, the device is arranged and configured to training the data set by: receiving audio samples from healthy subjects; framing the received audio samples so as to provide stationary signals; extracting features from the framed samples so as to generate the train data set.

In an embodiment, the device is configured and arranged to execute the peak valley method used to determine respiration data by: receiving an input signal indicating respiration; processing the received signal with a low pass filter so as to provide a smoothed respiration signal; and based on the smoothed respiration signal extracting parameters associated with the respiration.

In an embodiment, the device is arranged and configured to execute the method of the first aspect of the present description.

According to a third aspect of the present description, there is provided a system for measuring the acoustic response from a baby during a selected time period to provide acoustic information; the sensor comprising: a connector for connection to a monitor or display and a probe for engagement with a baby in use, wherein the connector comprises: a connector housing having a first part and second part, wherein the first part has a fixing projection for engagement with a fixing recess on the second part to connect the first and second parts; circuitry to enable electronic connection to an external component; one of the first and second parts having one or more central projections arranged to project from an inner surface thereof and engage with one or more corresponding recesses on the other of the first and second part, wherein the positioning of the or each projections and recesses are selected to enable avoidance of the circuitry within the connector housing.

In an embodiment, the fixing projection of the first part comprises one or more longitudinal projections and the fixing recess on the second comprises a correspondingly sized longitudinal slot for receipt of the one or more longitudinal projections.

In an embodiment, the connector housing is generally rectangular in plan view and the or each of the fixing projections for engagement with the or each of the fixing recesses are arranged generally along edges of the rectangle.

In an embodiment, the probe for engagement with a baby in use, is formed of a probe bottom for contact and engagement with a baby's skin in use, the bottom having a central region for receiving a microphone and an opening for unobstructed travel of sound/air from the baby to the microphone.

In an embodiment, the central region includes a recess in a bottom surface thereof shaped to house a microphone.

In an embodiment, the opening is positioned within the recess.

In an embodiment, the system comprises a peak valley detector for detection of movement of a baby to infer therefrom breathing patterns of the baby.

In an embodiment, the peak valley detector comprises a micro pressure cuff for measurement of variation in pressure from a respiring baby.

According to a fourth aspect of the present description, there is provided a system for executing the method of any of the features of the first aspect of the present description.

According to another aspect of the present description, there is provided a method for monitoring feeding maturation in premature babies, the method comprising; measuring the acoustic response from a baby during a swallow cycle to provide acoustic information and comparing the measured response against a data set to determine an indication of a swallow event; measuring the respiration pattern of the baby during the swallow cycle using a segmented peak and valley model to provide respiration information; and, in dependence on the provided swallow and respiration data determining a feeding maturity of the baby.

In one example, the step of measuring the acoustic response from a baby during a selected time period comprises extracting features from a received signal and comparing the extracted features against the data set.

In one example, prior to the step of extracting features, a received signal is framed so as to be considered as stationary.

In one example, the comparison against the set comprises comparing extracted features in a classification process.

In one example, feature extraction is performed using a speech analysis tool.

In one example, the feature extraction comprises labelling identified features as one or more of features selected from the group including:

i. swallow sound
ii. final discrete sound
iii. respiration sound
iv. other non-swallow sounds such as vowel, pleasure or crying.

In one example, training of the data set comprises: receiving audio samples from healthy subjects; framing the received audio samples so as to provide stationary signals; and, extracting features from the framed samples so as to generate the train data set.

In one example, the peak valley method used to determine respiration data comprises: receiving an input signal indicating respiration; processing the received signal with a low pass filter so as to provide a smoothed respiration signal; and based on the smoothed respiration signal extracting parameters associated with the respiration.

In one example, the parameters include one or more of breath rate, and onset or end of an inspiration or expiration event.

In a further aspect of the present description, there is provided a device for monitoring the feeding maturation in a premature baby, the device comprising; a sensor for measuring the acoustic response from a baby during a selected time period to provide acoustic information; a sensor for measuring the respiration pattern of the baby during the swallow cycle; and a processor the processor being arranged and configured to compare the measured acoustic response against a train data set to determine an indication of a swallow event; and being arranged and configured to use a peak and valley model to provide respiration information based on the measured respiration pattern; wherein, in dependence on the provided swallow and respiration data a feeding maturity of the baby can be determined.

Preferably the device is arranged and configured to execute the method of any of the features of the first aspect of the present description.

In an example, the device is arranged and configured to training the data set by: receiving audio samples from healthy subjects; framing the received audio samples so as to provide stationary signals; extracting features from the framed samples so as to generate the train data set.

In an example, the device is configured and arranged to execute the peak valley method used to determine respiration data by: receiving an input signal indicating respiration; processing the received signal with a low pass filter so as to provide a smoothed respiration signal; and based on the smoothed respiration signal extracting parameters associated with the respiration.

BRIEF DESCRIPTION OF THE DRAWINGS

Embodiments of the present description will now be described in detail with reference to the accompanying drawings, in which.

DETAILED DESCRIPTION

This description provides a method for monitoring feeding maturation in premature babies. As will be explained in greater detail below, the method includes measuring an acoustic response from a baby during a swallow cycle to provide acoustic information and measuring the respiration pattern of the baby during the swallow cycle. The received data is then used in a novel and inventive way and processed so as to provide previously unavailable detail and understanding related to babies feeding maturity. Specifically, and as will be explained in detail below the method requires comparing the measured acoustic response against a data set to determine an indication of a swallow event and use of a segmented peak and valley model to provide respiration information based on the measured respiration data. Subsequently, in dependence on the provided swallow and respiration data it has been determined that information relating to the feeding maturity of a baby can be obtained.

In addition, this description provides a means of capturing data reliably that in turn makes it possible to calculate a maturity-related parameter using both swallow and respiration signal. The "inspiration after swallow count" indicates the number of inspiration events occurred just after the swallow event is finished. The higher the value of this parameter the poorer the oral feeding skill of the baby. See for example, Lau, C., Smith, E. O., & Schanler, R. J. (2003). Coordination of suck-swallow and swallow respiration in preterm infants, Acta Paediatrica, 92(6), 721-727.

The various steps in the processing and an overview of the method and suitable apparatus for implementation thereof will now be described in detail.

Figure 1:
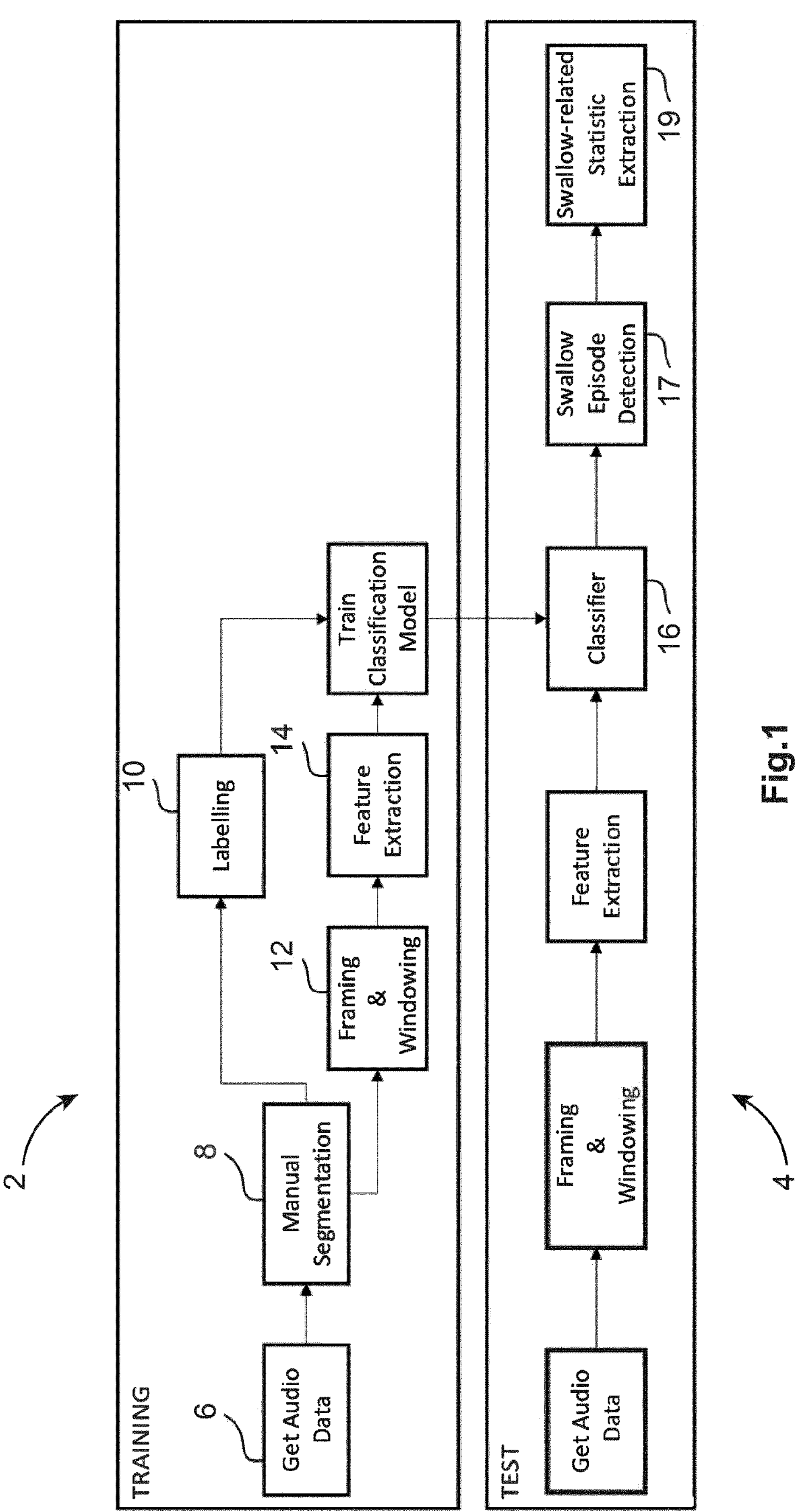
FIG. 1 shows a schematic representation of a training and test algorithm for use in a method of extracting swallow-related statistics.

Swallow Data Processing in order to detect swallow sound segments of infant subjects automatically with the help of machine learning algorithms, a data driven-system is utilised. FIG. 1 shows a schematic representation of a training and test algorithm for use in a method of extracting swallow-related statistics.

Referring to FIG. 1 a training phase 2 and a test stage 4 are shown in block diagram format. To perform the training stage 2 observation data 6 is collected from a number of healthy subjects including preterm and term newborns. For that reason, acoustic feeding signals which are sampled, typically at 22,050 kHz are acquired via the recording hardware.

Typically, the length of each feeding signal is selected at two minutes and can be extended or shortened if needed. Each feeding recording is captured 6 in a quiet environment with a swallow sensor probe and monitor or computer system as will be described in greater detail below. The sensor may be held to the hyoid region of a healthy infant subject. In addition to feeding recordings, text files including the beginnings of the swallow events for each baby are available. These text files are generated and written during the feeding session by software. The sampling is typically done in the presence of a trained technician or doctor who is able to watch and listen as the signals are recorded. Each time a swallow event occurs, the specialist doctor or technician or other trained observer, is required to record it by, for example clicking a mouse so as to specify or indicate within the two minutes of recording sessions when the swallow event(s) occurred.

Then, audio and text files are analysed subsequently to correct possible time synchronization mismatches. The received signal is then preferable manually segmented 8 into shorter time interval signals for subsequent processing. Manual segmentation is applied around the instants of sound activities.

Labelling

Next, manually segmented signal undergoes a labelling process 10. The labelling may be done using any known speech analysis tool. One useful and widely available example is the open source Praat tool, This will be described in greater detail with reference to FIGS. 5 to 9 which show data extracted from an acoustic feeding signal for use in determination of swallow events.

Examples of received audio signals are shown on the various traces of FIGS. 5 to 9, with labels applied as follows:

1. y: swallow sound label (swallow class)
2. fds: final discrete sound label (non-swallow class)
3. rsp: respiration sound label (non-swallow class)
4. n: vowel, pleasure or crying sounds label (non-swallow class)

Figure 5:
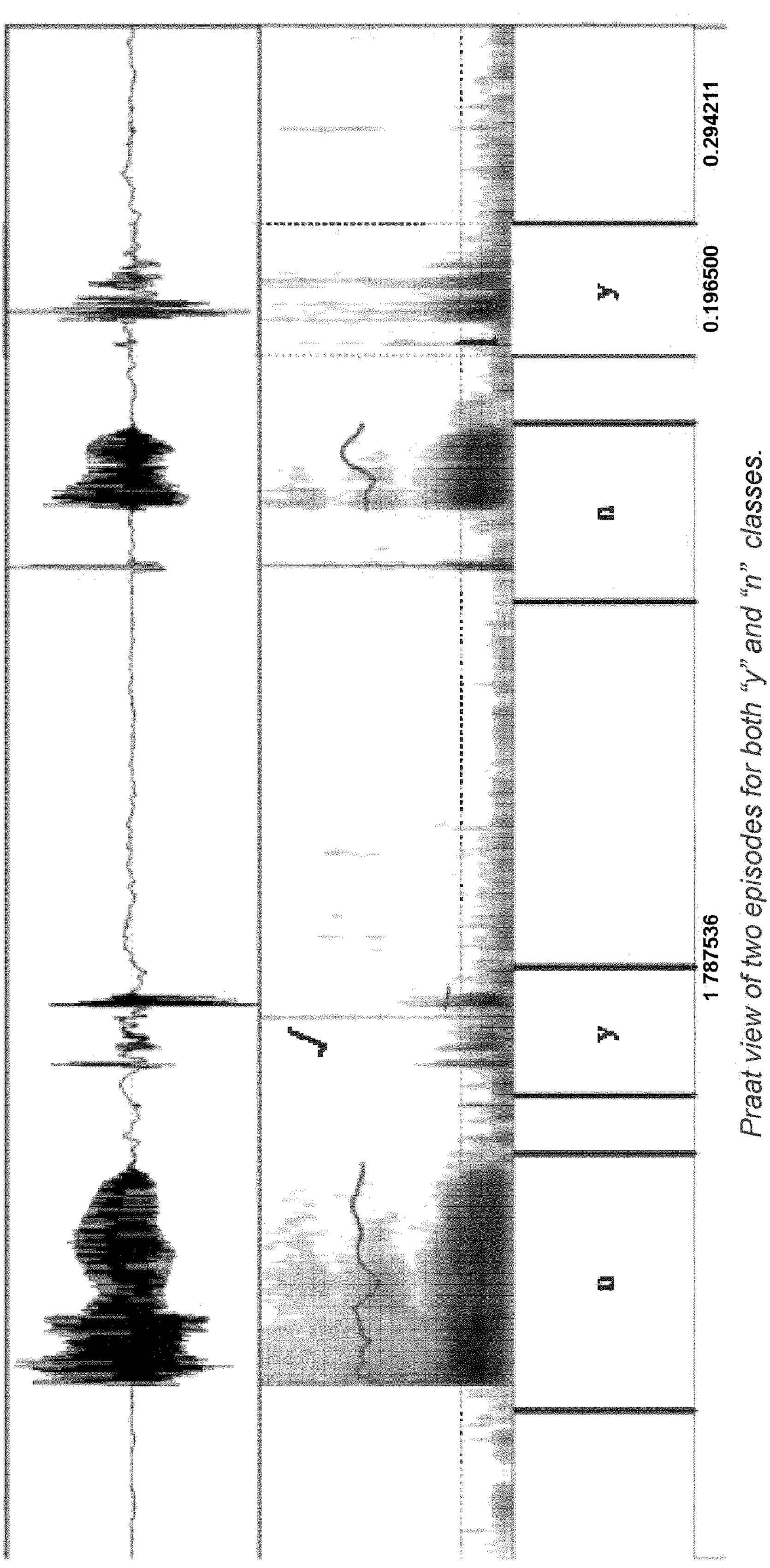
FIGS. 5 to 9 show raw data extracted from an acoustic feeding signal for use in determination of swallow events.
Figure 6:
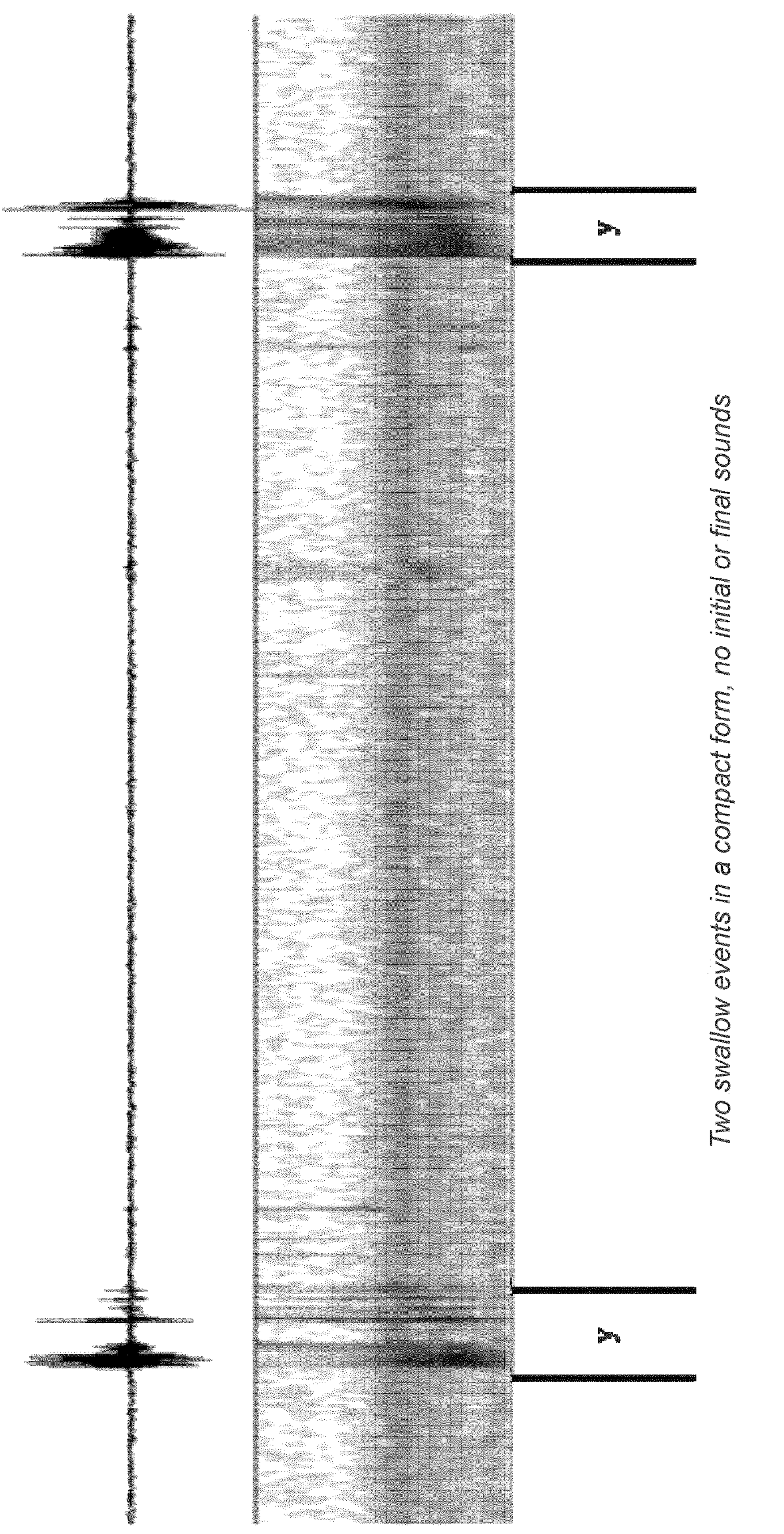
Figure 7:
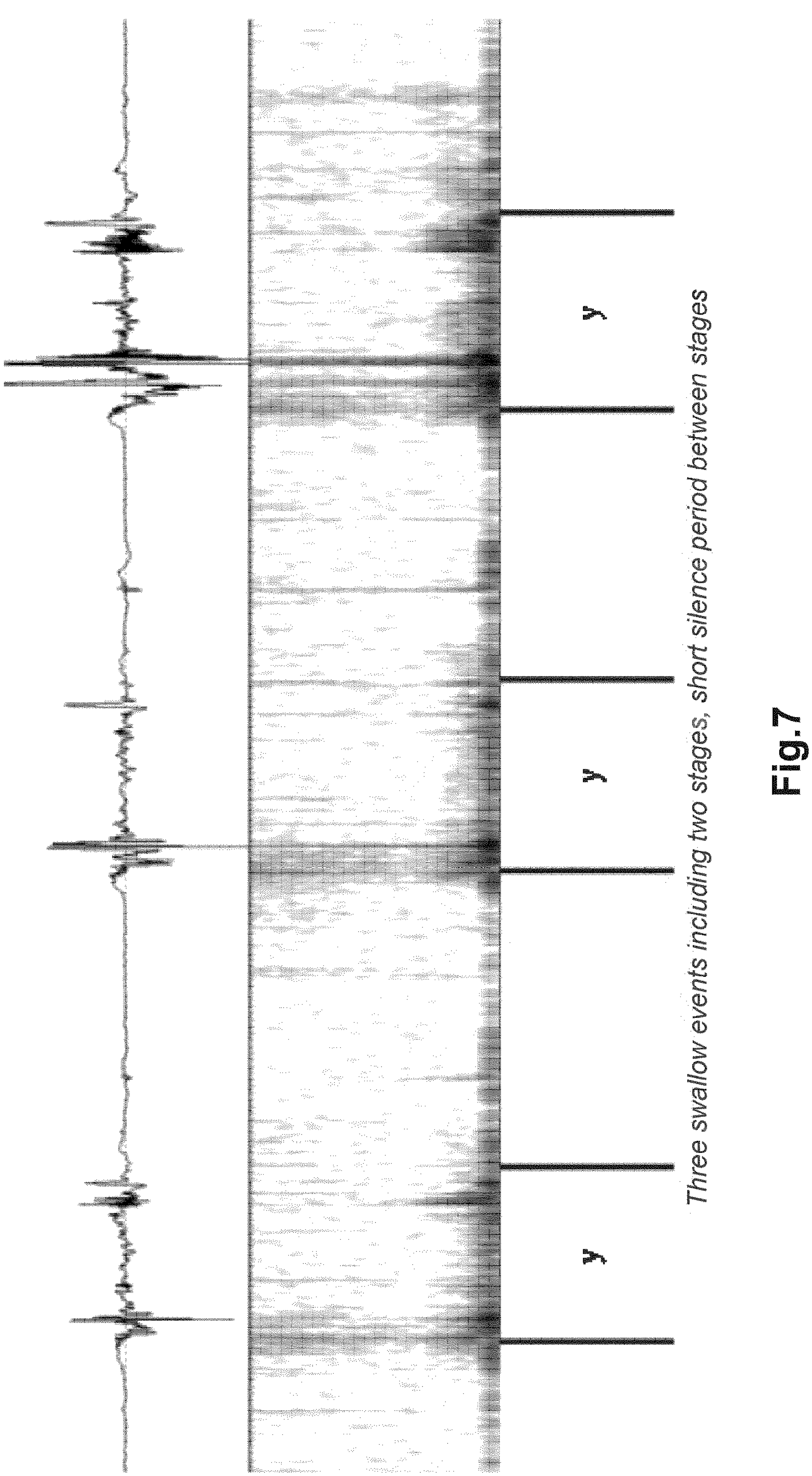
Figure 8:
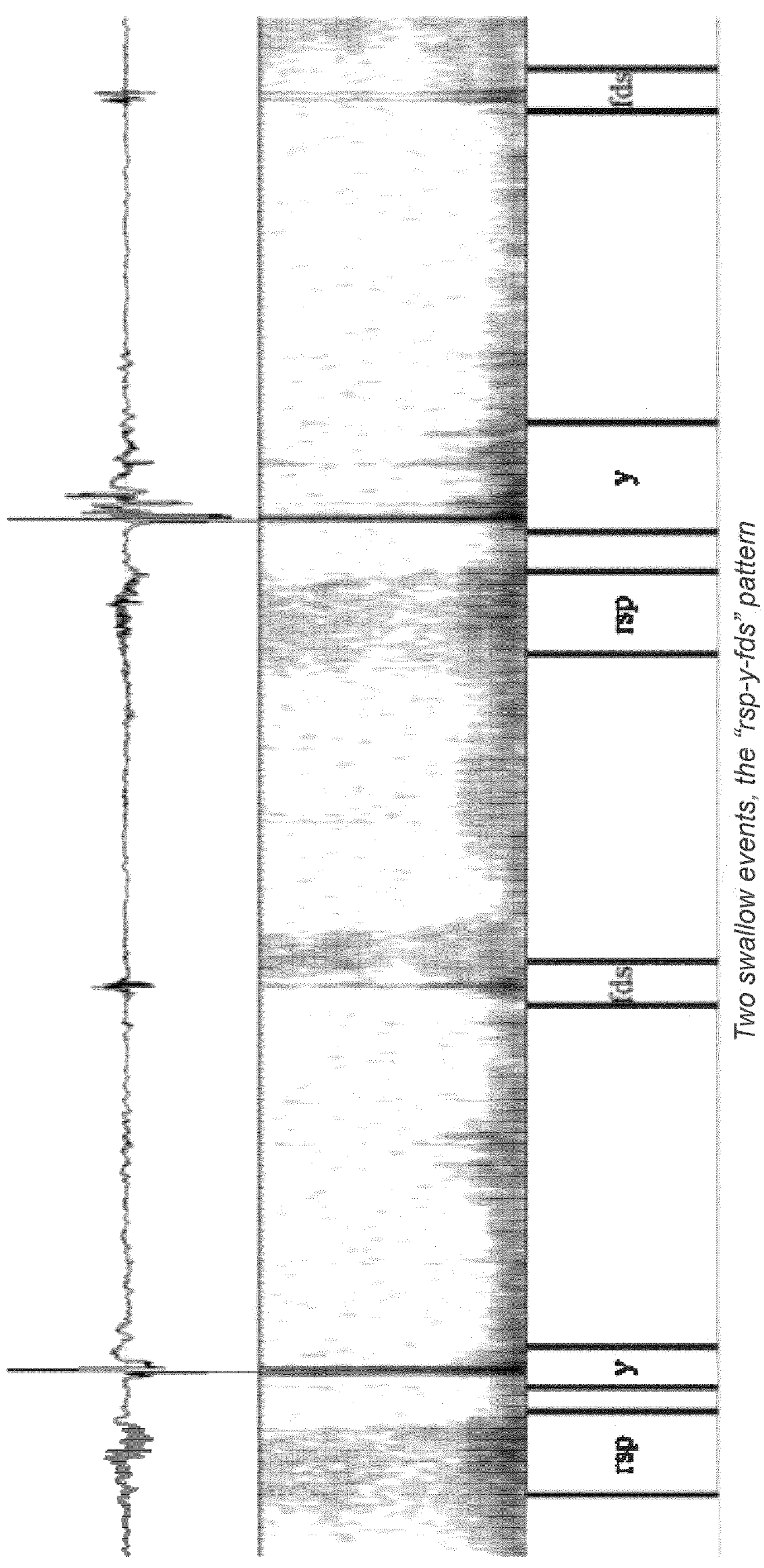
Figure 9:
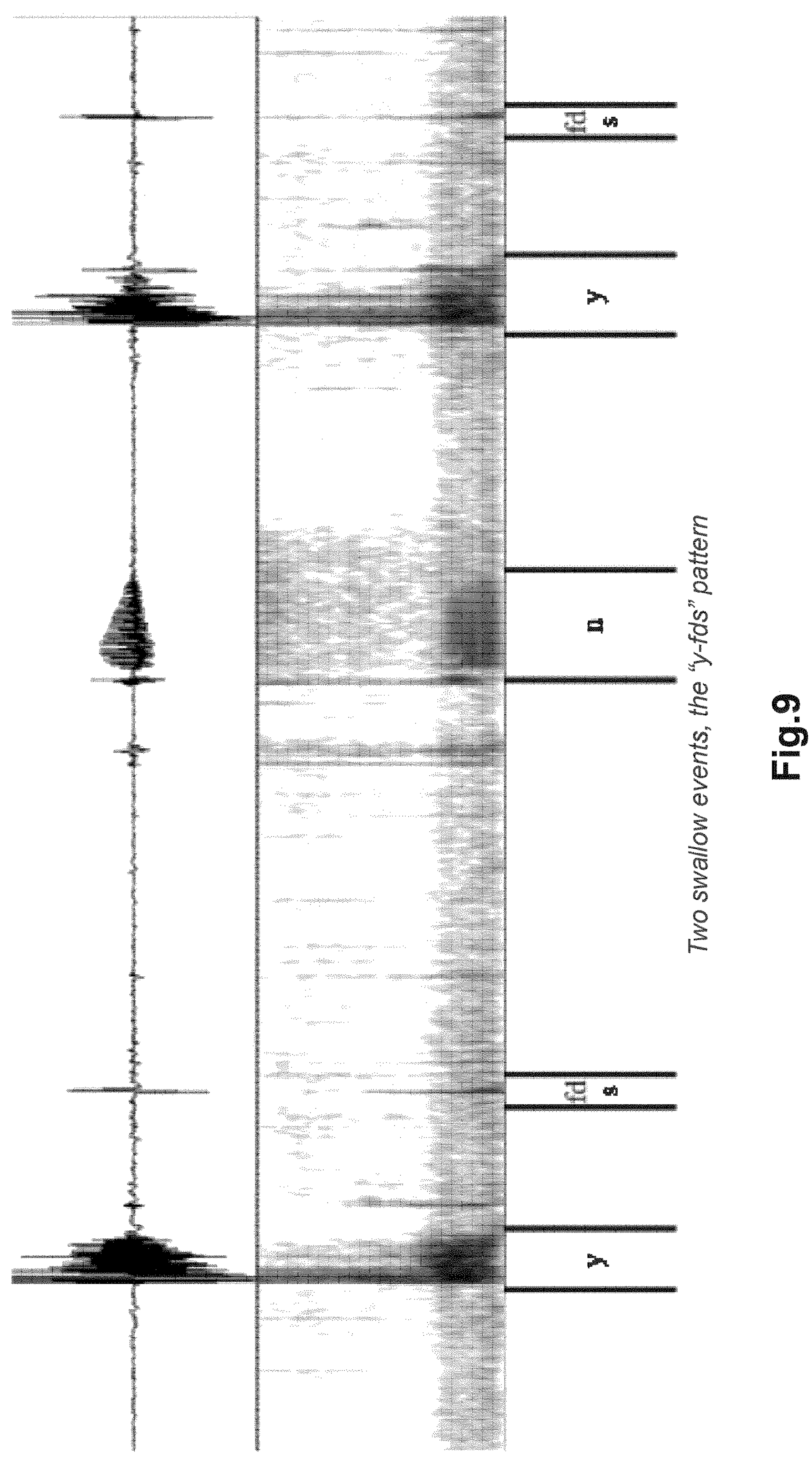

Accordingly, in addition to swallowing events labelled as 'y', several non-swallow sound activities were observed and they were labelled as 'n' (non-swallow) as indicated in FIG. 5. Even though there are similarities, not all the swallowing sounds obey a particular signal pattern.

Three terms related to the swallowing process are defined in the previous studies which are an initial discrete sound (IDS), a bolus transit sound (BTS) and final discrete sound (FDS). Here in the examples shown, it is observed that there are similar sequences of such activities, but the presences of FDS and DS are not guaranteed. Besides, inspiration and expiration sounds may appear before or after the bolus transmission event. However, BTS is considered to be permanent which is why only it was labelled as a swallow interval.

in FIGS. 6 to 9, four different swallow sound patterns are indicated.

Framing & Windowing

Swallow sounds are assumed to be non-stationary signals. For this reason, the entire feeding signal is divided 12 into small frames so that the signal in a frame can be considered as stationary. A Hamming or other such windowing function is applied to frames to suppress edge discontinuities and diminish spectral leakage due to the framing process.

Then, Discrete Fourier Transform of each Hamming windowed frame is computed to extract spectral-domain features.

Feature Extraction

Features are then extracted 14 from the frames as will be described below.

1. Spectral Centroid

A spectral centroid is identified for each frame. It is the centre of mass of the Fourier transform of a signal frame and may be calculated or determined using the following formula:

$$C_{x_i} = \frac{\sum_{k=0}^{L-1} k\left|F_{x_i}[k]\right|}{\sum_{k=0}^{L-1} \left|F_{x_i}[k]\right|}$$

In which Fxi represents the DFT of xi.

2. Mel Frequency Cepstral Coefficients

The human ear can be considered as a filter concentrated non-uniformly on specific regions of the frequency spectrum. Since the frequency discerning skill of the human ear decreases with increasing frequency, the low-frequency region contains more filters than the high one.

Figures 2, 3:
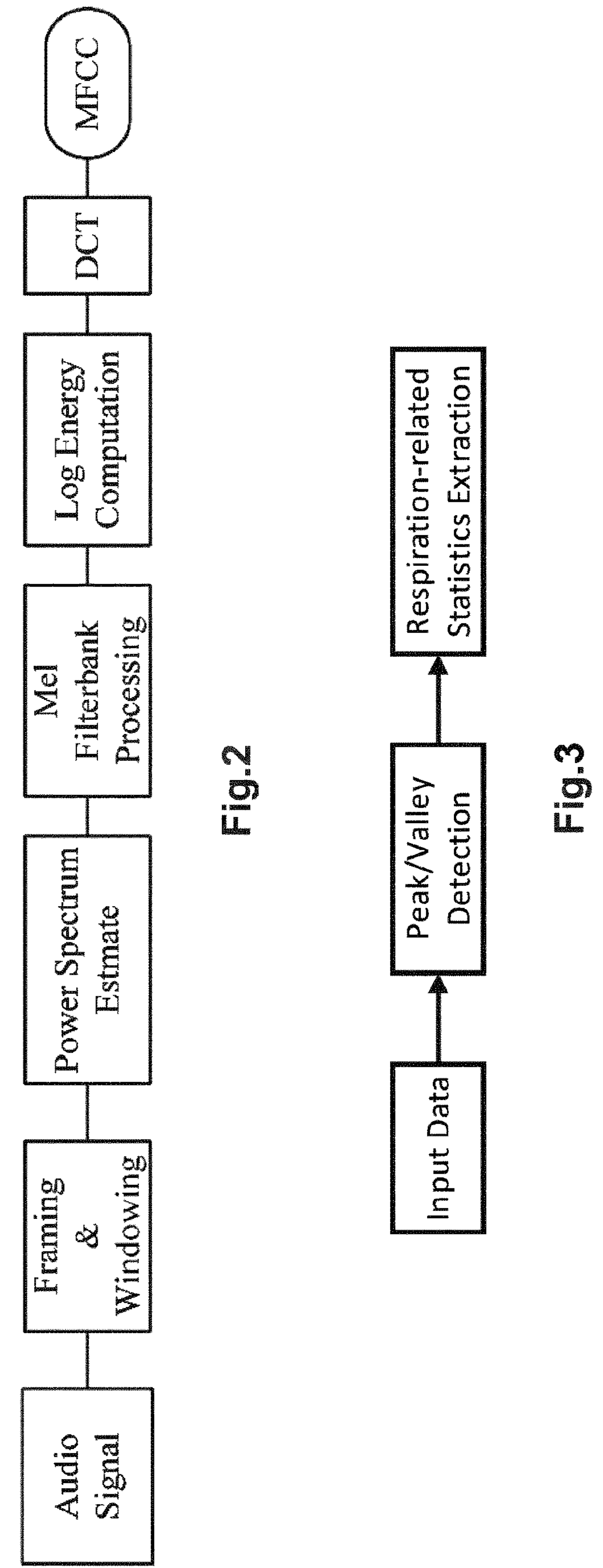
FIG. 2 shows an example of mel frequency cepstral coefficient pipeline.
FIG. 3 is a schematic representation of a pipeline of a process for the extraction of respiration-related statistics.

For the same reason, the perception of the human auditory system cannot linearly evaluate pitch in terms of a frequency (Hz) scale. To approximate this perception, Mel frequency is utilized to extract features. Mel Frequency Cepstral Coefficients (MFCC) are derived from that logic and have dominated the speech and audio processing field for a long time thanks to their ability to represent audio signals in a compact form. The pipeline for calculation of MFCC is shown in FIG. 2.

Training Via SVM

Once features have been extracted at step 14, the classification derived from the measured signals is trained. As is well known, support-vector machines (SVMs), are an example of a supervised learning models with associated learning algorithms that analyse data and can be used for classification and regression analysis. Given a set of training examples, each marked as belonging to one or the other of two categories, an SVM training algorithm builds a model that assigns new examples to one category or the other.

In the present method, two different SUM-based classification models are built.

In the Binary SVM Classifier case, the swallow represents one class, whereas the combination of non-swallow and silent parts constitutes the other class. Moreover, the swallow frame features are labelled as "0" and, concatenated silent and non-swallow frame features as "1". After applying, min-max normalization, the training model is built with the help of binary SVM optimization.

Although SVM is inherently a binary classifier, multi-class problems can be solved with one-versus-all (OVA) strategy. In this case, for example, let K be the number of classes, then K binary classifiers are trained in the OVA method.

In other words, each class has its own classifier in which instances belonging to that class is labelled as positive and the rest as negative. Based on this, silence features are separated from the non-swallow ones and treated as another class, thus, increasing the number of classes from two to three. After the silence features are labelled as '2', each classifier is trained separately with the same optimization technique. The system has now produced a trained classification model, which as will be described below can be used accurately and repeatably to identify swallow events in the actual test data. Clinician input has been used at the start of the process where swallow events within the received samples 6 were identified and labelled 10, but from this stage it is possible for the swallow event identification and classification of an actual test 4 to be performed automatically.

In FIG. 1, the test sequence 4 is shown schematically and it can be seen that it includes steps of receiving audio data, framing and windowing and feature extraction which correspond or are the same as those steps described above with respect to the training process 2. However, the step 16 of classification will now be described in detail.

Classifier

A classifier step 16 functions within the test 4, to operate on received audio data that has already been framed and windowed and had features extracted as described above with reference to the training process 2.

In this stage 16 of the test, normalized frame features are given as input to the SVM models built in the training 2 of the process. In the binary SVM case, posterior probability values of the swallow and non-swallow class are obtained for each frame. On the other hand, classifier outputs of the frames will be three distinct score values in the multi-class case.

Swallow-Episode Detection

This module 17 is for determination of swallow event boundaries by merging the frame outputs of the output of classifier stage 16.

1.2-Class Finite State Machine (FSM2cls)

The input is a binary vector obtained by thresholding the probability estimate values of each frame. The number of ones, consecutive ones and the number of zeros are taken into consideration to determine the boundaries of swallow action.

2.3-Class Finite State Machine (FSM3cls)

Let N be frame number of an acoustic signal obtained from a feeding session, then the input for the FSM algorithm will be N×3 matrix including frame probability values for each class. Swallow and non-swallow frame count and threshold for each class are used as inputs to implement this algorithm.

Figure 10:
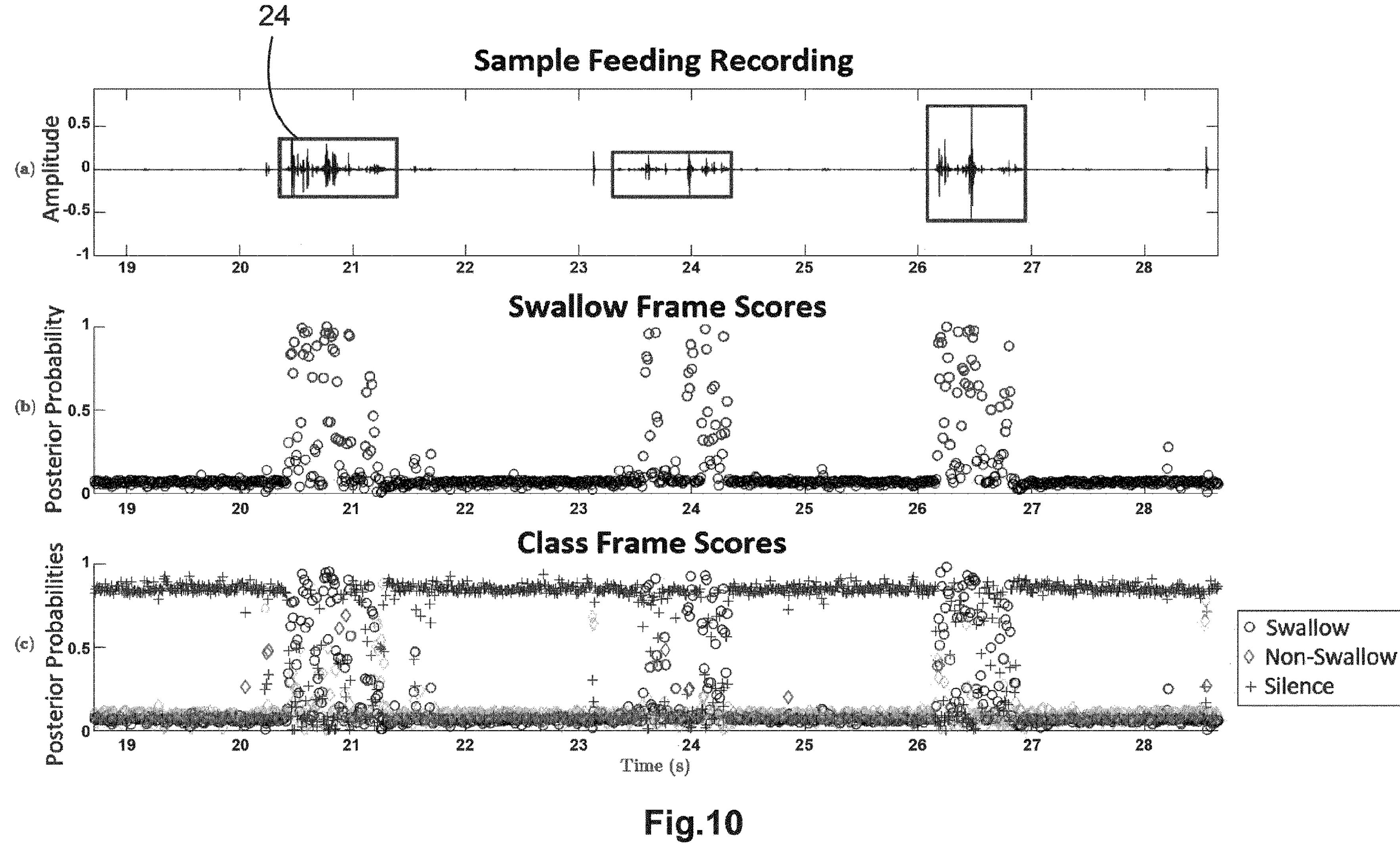
FIG. 10 shows a selection of feeding signals representing three swallow activities.

In FIGS. 10(*a*) to 10(*c*), a portion of a sample recording with three swallow instants is shown. As can be seen in FIG. 10(*a*), three boxed swallow events 24 can be seen. FIGS. 10(*b*) and (*c*) show respectively the corresponding posterior probabilities (confidence score) for both the 2-class and 3-class types of classifiers.

Figure 11:
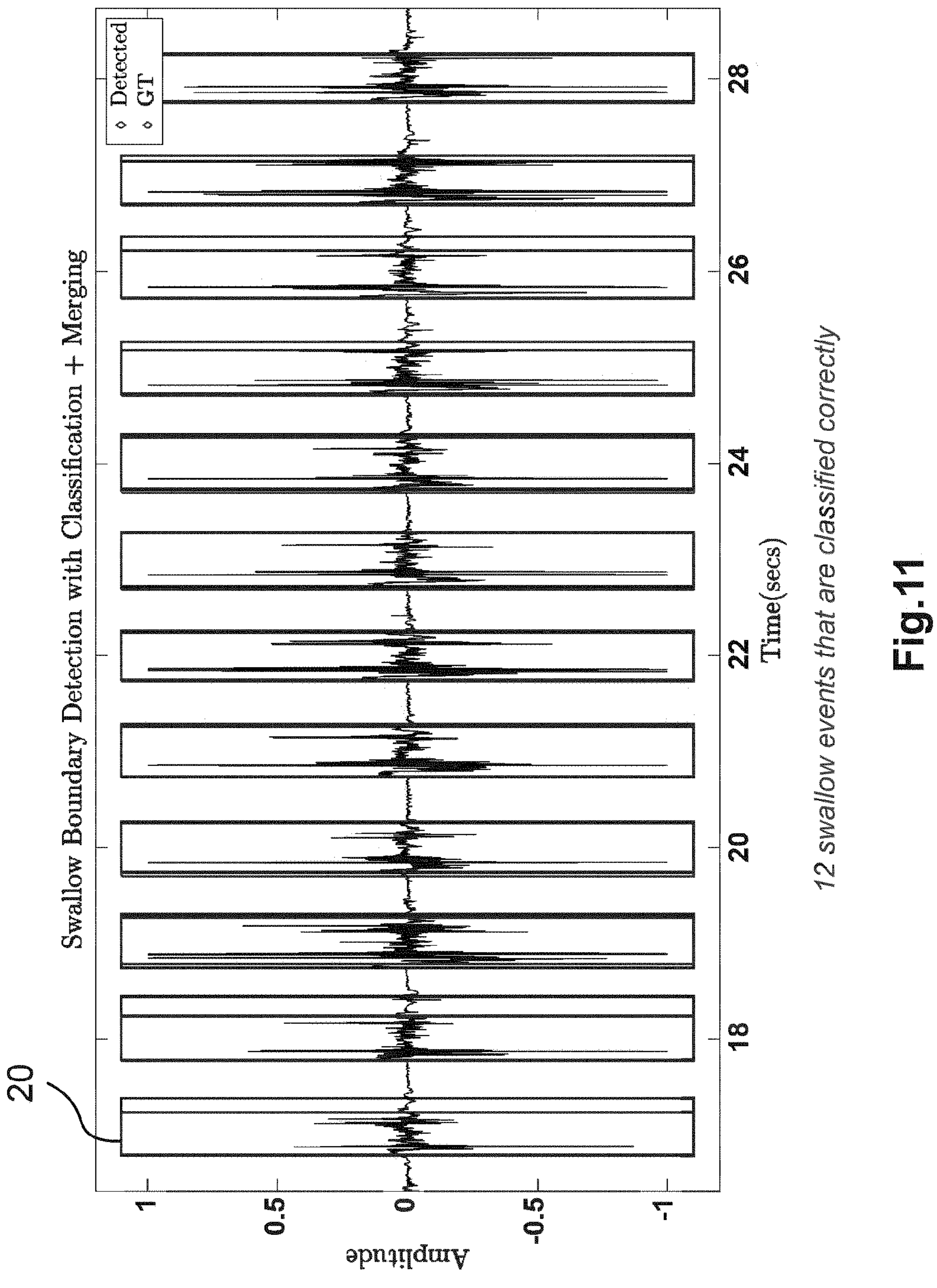
FIGS. 11 and 12 show result scenarios determined from swallow data.
Figure 12:
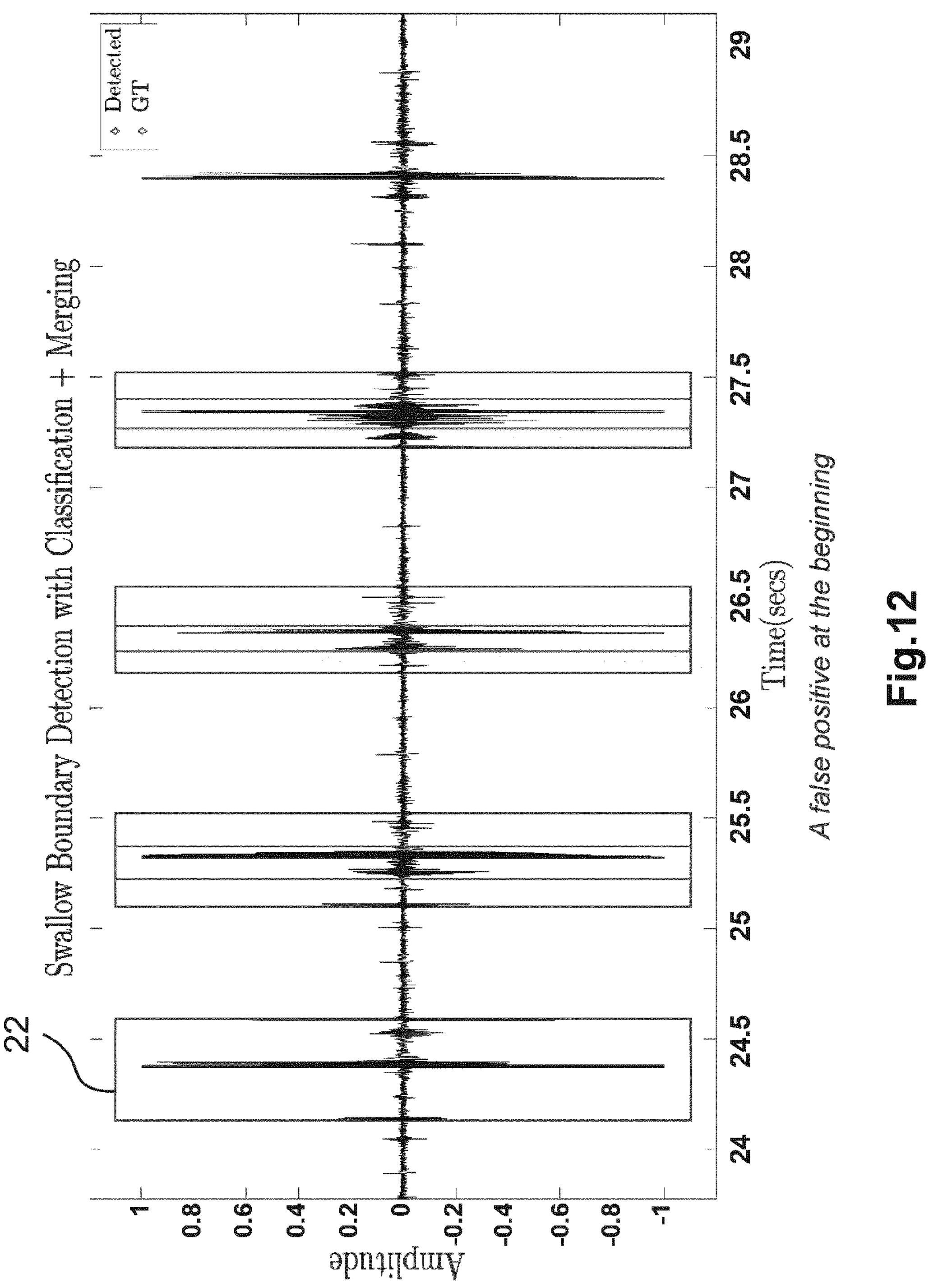

In FIGS. 11 and 12, two different result scenarios are depicted. In FIG. 11, the detection system performed successfully in identifying swallow events 20, whereas for the sake of example FIG. 12 shows a situation in which a false positive 22 is recorded.

Swallow-Related Statistics Extraction

Next at step 19 swallow-related sounds of new-born infants are associated with the feeding maturity of infants using different digital signal processing techniques. It has been recognised through experimental findings that post-menstrual age (PMA) and the average time between rhythmic swallows have a negative correlation. In addition, an increase in the maximum number of rhythmic swallows refers to the development of feeding skills of infants. See for example any of Vice, F. L, Bamford, O., Heinz, J. M., & Bosma, J. F. (1995). CORRELATION OF CERVICAL AUSCULTATION WITH PHYSIOLOGICAL RECORDING DURING SUCKLE-FEEDING. IN NEWBORN INFANTS. *Developmental Medicine & Child Neurology,* 37(2), 167-179; Gewolb, I. H., Vice, F. L., Schweitzer-Kenney, E. L., Taciak, V. L., & Bosma, J. F. (2001).

Developmental patterns of rhythmic suck and swallow in preterm infants. Developmental medicine and child neurology, 43(1), 22-27; or Ince, D. A., Ecevit, A., Acar, B. O., Saracoglu, A., Kurt, A., Tekindal, M. A., & Tarcan, A. (2014). Noninvasive evaluation of swallowing sound is an effective way of diagnosing feeding maturation in new-born infants. Acta Paediatrica, 103(8), e340-e348

In the present method at steps 17 and 19, the swallow events are detected from the feeding sound and from identification of an event or plural events within a sample it is possible to determine data relating the swallow performance of the baby during the test period. This in turn based on, for example, the papers above enables feeding maturity to be determined or data relating to feeding maturity to be processed and analysed. Examples of statistical data obtained from these segments includes the maximum number of rhythmic swallows, the average time between rhythmic swallows, and the total number of resting intervals within a sample.

Accordingly, a repeatable and reliable method is provided for determination of swallow related statistics is provided. The process by which respiration data is obtained and processed will now be described below.

Respiration

Figure 13:
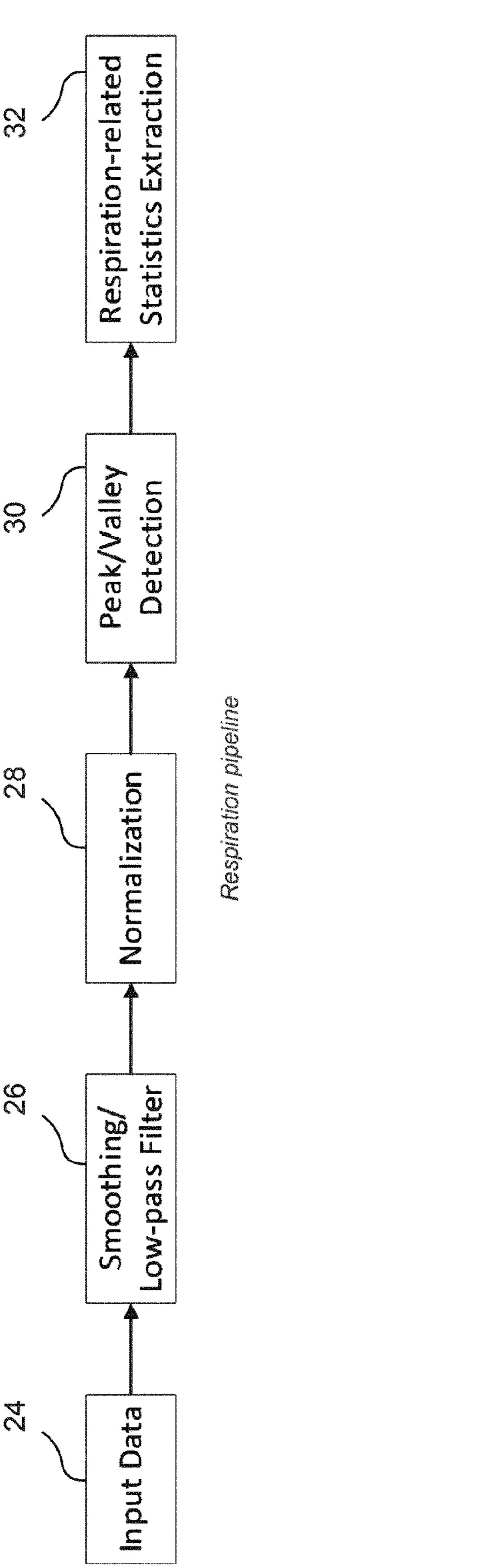
FIG. 13 shows a schematic pipeline for the process of reading and processing data from a respiration sensor.

The pipeline for reading and processing the data from the respiration sensor is shown in simplified form in FIG. 3, As can be seen input data is received from a sensor, to be described in greater detail below, and this is provided to a peak/valley detection mechanism extracting the respiration-related statistics. FIG. 13 shows a more developed model of a similar process. In addition to the steps above, as can be seen between the input of data 24 a smoothing low-pass filter 26 is provided. This in turn, provides an input to a normalization function or processor 28 before the steps of peak/valley detection 30 and respiration-related statistics extraction 32.

Peak/Valley Detection

Referring back to FIG. 4 a more detailed description of the process is now provided.

In addition to segmentation of swallow episodes, as already described above, the onsets and ends of respiration-related events, e.g. inspiration and expiration, are also detected. Typically, a respiration sensor is provided which is attached in some appropriate way to an infant's abdominal region. During respiration, it is recognised that muscle movements in the diaphragm (or chest) of the infant will generate peaks and valleys in a digitized respiration sequence. Accordingly, the inventors have here recognised that identification and categorisation of a respiration event can be considered as a peak or valley detection problem in a one-dimensional time series.

For this purpose, an adaptive threshold method may be used, such as one similar or the same as that described in Shin, H. S., Lee, C., & Lee, M. (2009), Adaptive threshold method for the peak detection of photoplethysmographic waveform published in Computers in biology and medicine, 39(12), 1145-1152, to detect peaks and valleys with minor modifications.

Figure 4:
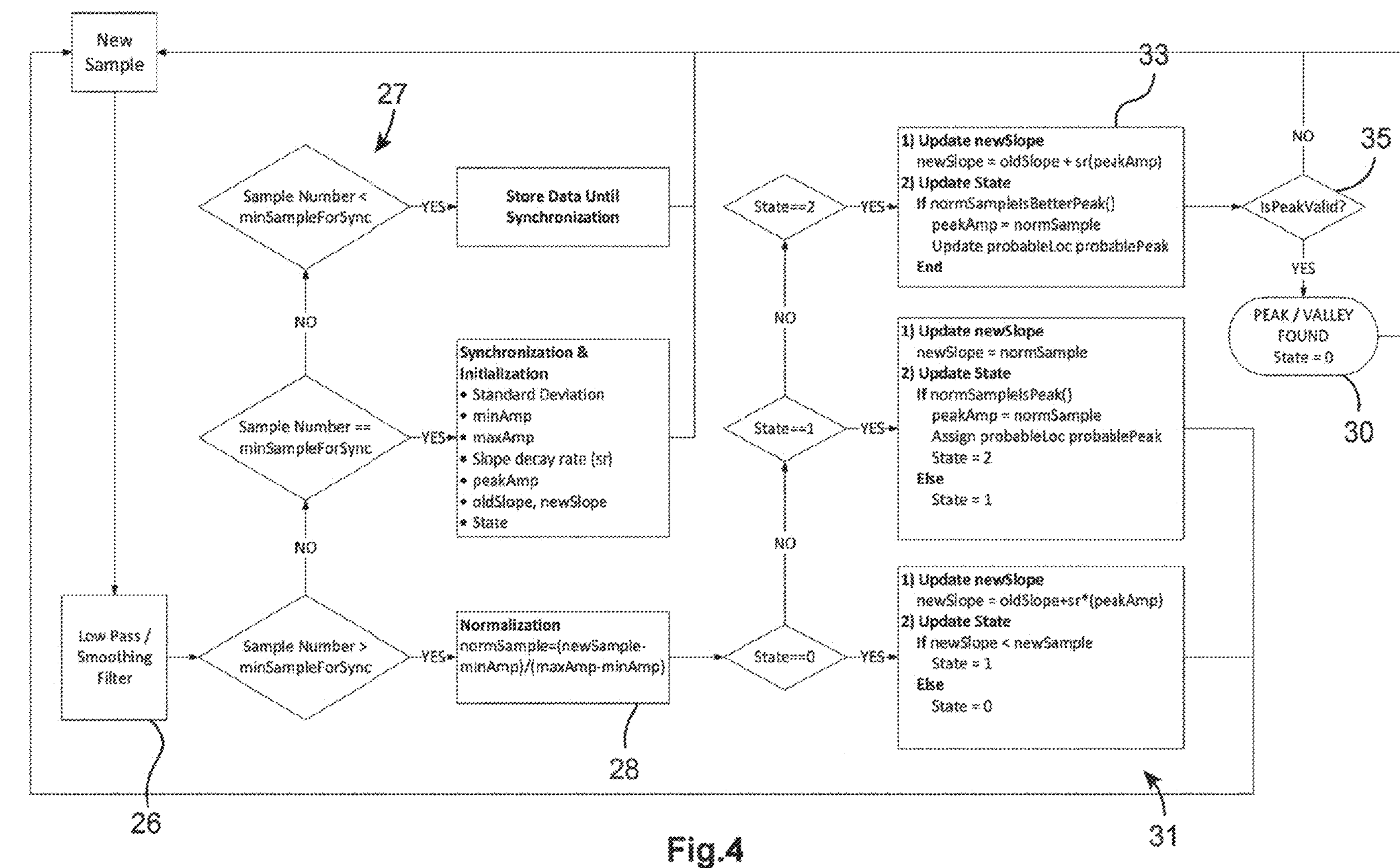
FIG. 4 is a flowchart showing the steps in an adaptive peak detection algorithm for use in determining respiration statistics.

The flowchart of the algorithm is given in FIG. 4.

As can be seen from inferred from the flowchart, firstly, the incoming respiration data stream is smoothed 26 with the help of moving average filter. A filtration such as one described in S. W. Smith et al., "The scientist and engineer's guide to digital signal processing," 1997 may be used. At step 27 the filtered values are stored in the memory until the synchronization parameters (the maximum and the minimum values of stream) are calculated and satisfy some defined threshold.

Then, at step 28 a normalization procedure is applied for each new incoming sample. Next, a finite state machine algorithm is utilised to characterise the received signal into one of three states. An example of an algorithm that can be used may be found in Shin, H. S., Lee, C., & Lee, M. (2009). Adaptive threshold method for the peak detection of photoplethysmographic waveform. Computers in biology and medicine, 39(12), 1145-1152 is applied to extract peaks/valleys. In this case however, three different slope decay rates 31 are used which is a modification which serves to increase the robustness of the peak detection algorithm.

Finally, as can be seen, at step 33 it is determined that if state 2 was identified then the parameters of the slopes satisfy the requirement that a peak or valley is present. The parameters set or used to identify each of the three states 31 can be chosen to optimize the testing being performed or fixed at predetermined parameters.

The peak or valley is then validated and then, upon validation, a confirmation is provided at 30 that a peak or valley has been found. Validation in this context may refer to confirmation that an identified valley or peak is a true representation of a valley or peak in the signal. Many peak/valley points may be found, but preferably validation is included in which it is determined if the points remain a peak/valley for more than a certain duration. The certain duration can be set as required by the application.

Figure 14:
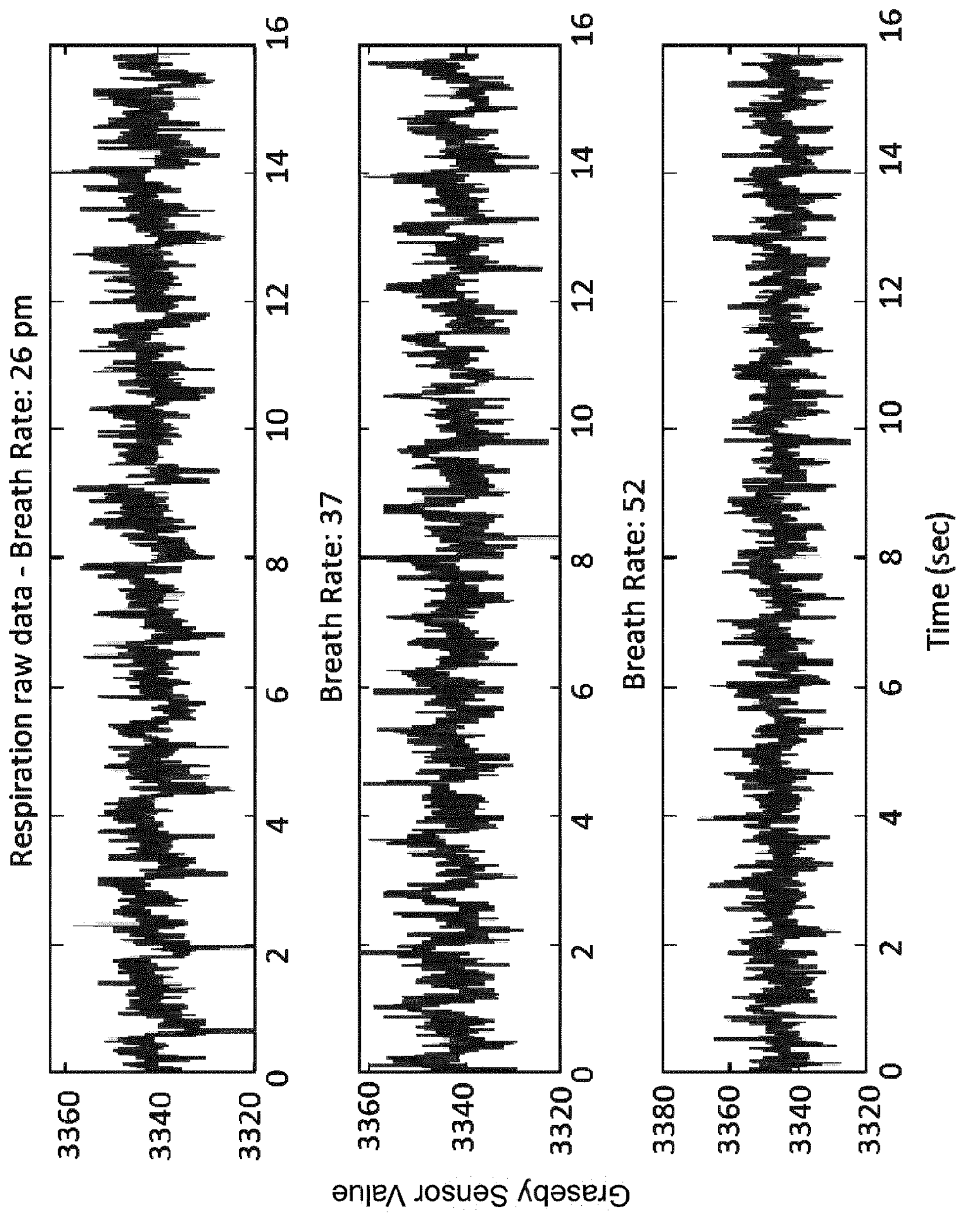
FIGS. 14 and 15 show examples of raw data representing the digitised respiration signal and a smoothed and normalised respiration signal derived therefrom.
Figure 15:
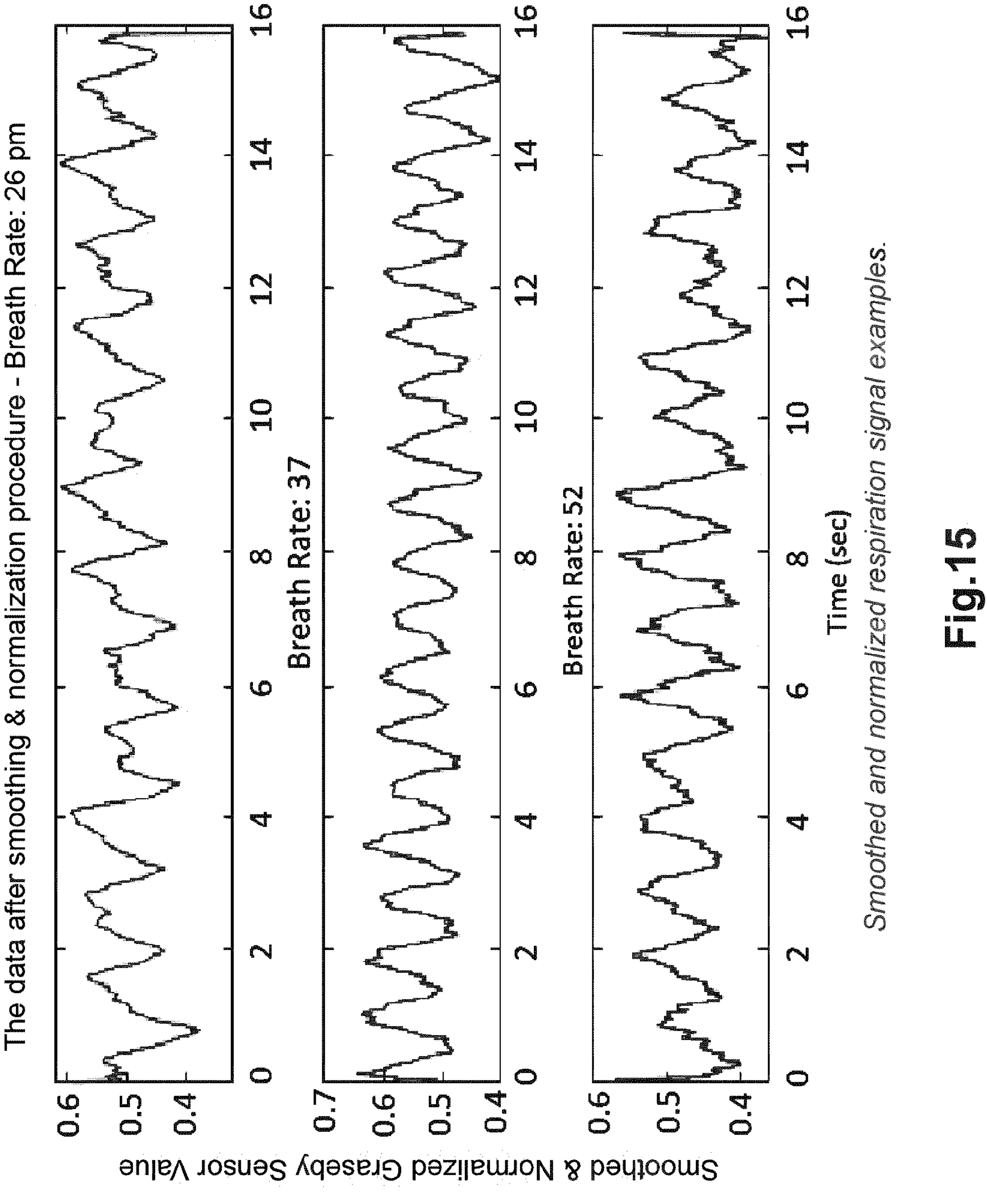
Figure 16:
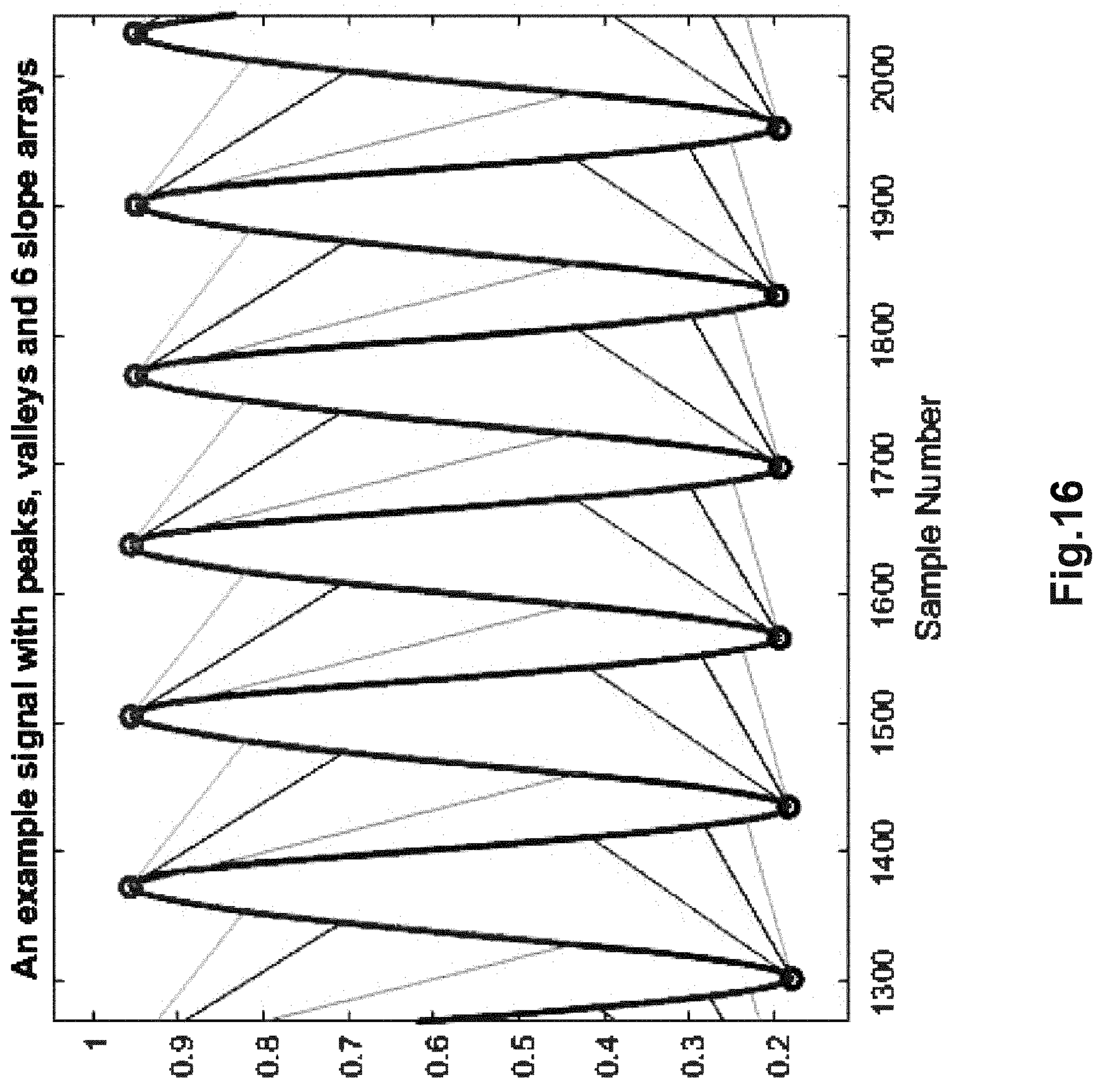
FIG. 16 shows an example of a peak and valley derived from the data of FIG. 15.

FIGS. 14 to 16 show three examples of the plotted raw data of 3 digitized respiration signals. The three signals are for respiration rates of 26, 37 and 52 breaths per minute, as indicated on the figures. As can be seen the signals are noisy, containing high frequency oscillations.

In order to segment inspiration and the expiration events of each of the respiration signals, firstly a smoothing process is applied, such that a smoothed signal is produced that can then be provided as an input to the min-max normalization. A smoothing process such as might be used at step 26 of FIG. 4 is applied. The output of the smoothing process for each of the signals of FIG. 14, can be seen, respectively in the three plots of FIG. 15.

In FIG. 16, an example signal with peaks, valleys and 6 slope arrays are illustrated. Peaks are shown with red circles whereas the valleys are the black ones. Additional 6 slope arrays (3 for peaks and 3 for valleys) are the variables that change depending on the respiration sensor output variation to help detect extrema points.

Although this visual does not show a problematic case, sometimes false peaks are detected if a slope-based algorithm is not employed. The values of those false peaks may be significantly smaller compared to the majority of peaks. In order to eliminate them, the slope algorithms are utilized. If at least 2 decaying slopes by-passes the small peaks, they can be eliminated.

Statistic Extraction

After the peak and valleys are extracted, the parameters associated with respiration may be determined or inferred therefrom. For example, parameters such as breath rate, and onset/end of inspiration/expiration events can be determined.

Hardware

Figure 17:
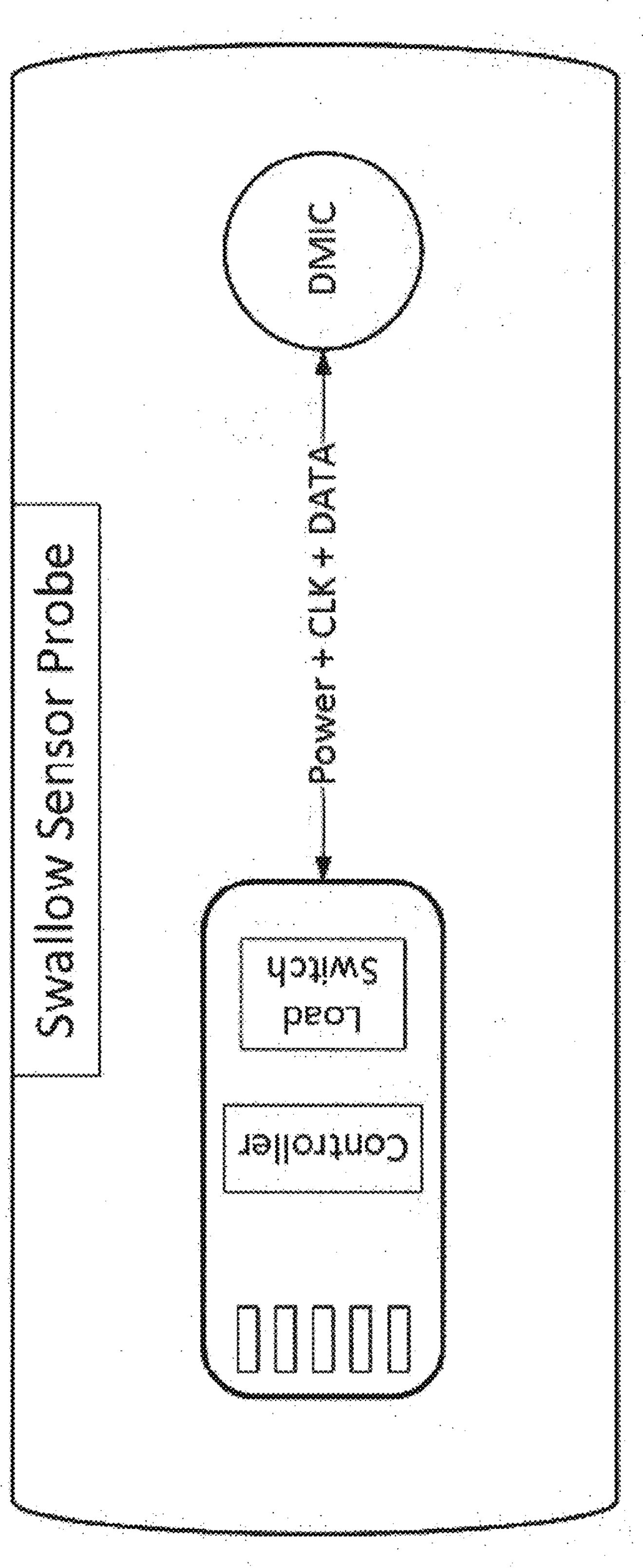
FIG. 17 shows a schematic representation of a swallow sensor probe.

Exemplary hardware will be described in detail below with reference to FIGS. 18B to 34. Schematically though, FIG. 17 shows a representation of a swallow sensor probe. As can be seen it includes a microcontroller unit with a load switch to power on/off the microphone sensor connected to the other end of the probe cable. The microcontroller has a built-in non-volatile memory that can be programmed by the microcontroller firmware over electronic means. The number of probes used is automatically interpreted by the microcontroller and stored in this non-volatile memory area. The load switch is inactivated by the microcontroller if the maximum number of uses of the probe is exceeded disabling the swallow sensor probe. Accordingly, it is possible easily to ensure that the probe is not used more than some defined number of times which can be important in health applications to ensure hygiene and accuracy are maintained.

Figure 18A:
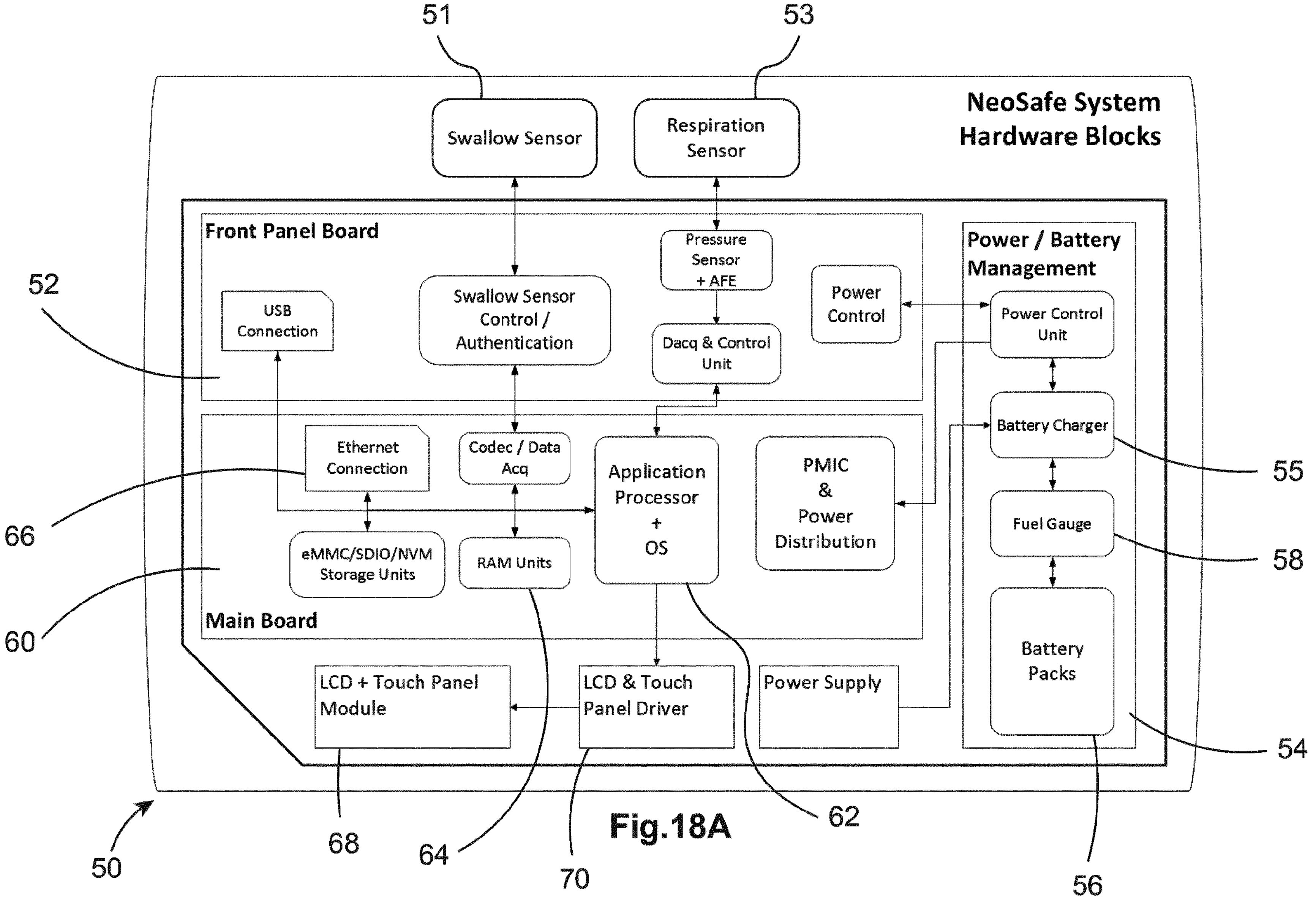
FIG. 18A shows a schematic representation of a system for the monitoring of feeding duration in infants.

FIG. 18A shows a schematic representation of a system for the monitoring of feeding in infants. The system 50 may typically be provided on a PCB or some other appropriate hardware means. In the schematic example shown a front panel board 52 is provided that acts as, amongst other things, an interface to external sensors and data sources 51 and 53 such as the swallow sensor probe shown in and described above with reference to FIG. 17. Respiration sensor 53 may, for example be provided by a micro pressure cuff arranged around a baby's chest.

A power/battery management board 54 is provided that includes components to ensure management of power distribution amongst components of the system. The power management board 54 preferably includes one or more battery packs 56 and an indicator or gauge 58 to display to a user the power level at any point in time. The battery pack can be rechargeable batteries and the system therefore optionally includes a battery charger 55 that is coupled to a power supply, which itself is capable of connection to an external power source for receipt of power.

A main board 60 is provided that includes a microprocessor 62 arranged and configured to perform the processing and calculations etc. that are described above with reference to any of FIGS. 1 to 16. As can be seen memory in the form of RAM units 64 are provided that are able to store data received from the sensors during processing. A described above with reference to FIG. 4, in the process of peak and valley identification based on respiration, during the receipt of data a storage function is provided to ensure that data can be stored until synchronised 27.

The system 50 is also preferably able to connect to an external network and therefore preferably includes an interface 66 such as an Ethernet connection. This enables remote control of the system and also transmission and communication of data from the system via a network such as the internet to a remote user.

User interface and communication systems are also provided in the form of an LCD touchscreen module 68. This enables a use to provide inputs and control signals to the system in use. A driver unit 70 is provided that couples the LCD touchscreen module 68 to the microprocessor 62. It will be appreciated that the hardware can be provided by any suitably configured or programmed processing circuitry. In one example the processor 62 is in the form of an ASIC.

Figures 18B, 19:
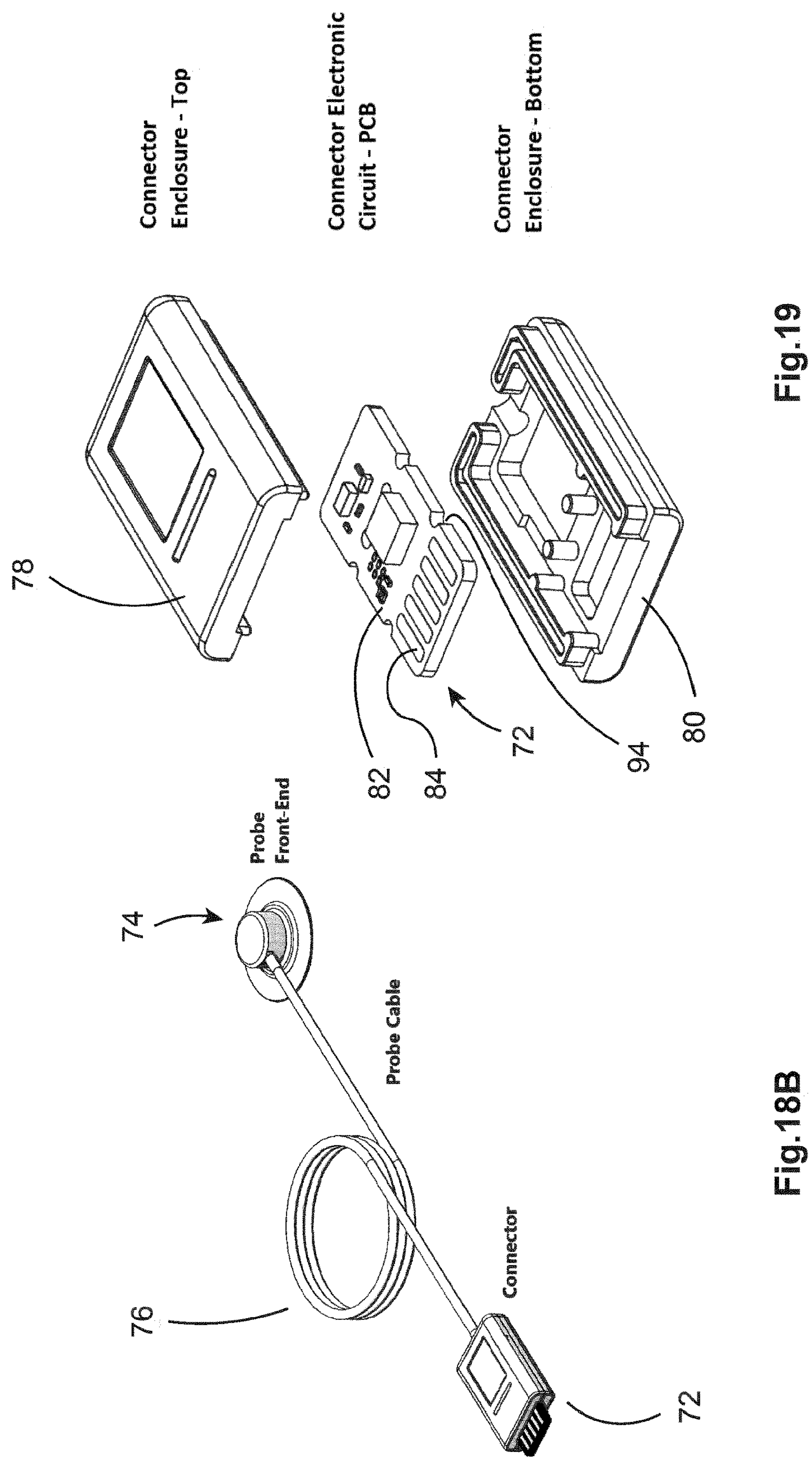
FIG. 18B is a schematic view of a swallow sensor probe.
FIG. 19 is a schematic view of the internal structure of connector assembly of the swallow sensor probe of FIG. 18.

FIG. 18B is a schematic view of a swallow sensor probe. The sensor probe includes a probe front end 74, a connector 72 and a connecting cable 76. Both the connector and the front-end parts contain electronic circuit boards that are used in detection of the swallow signals, as will be explained below and as already explained above with reference to FIG. 18A.

Referring then to FIG. 19, as mentioned above there is shown a schematic view of the internal structure of the connector 72 of the swallow sensor probe of FIG. 18B. The connector comprises a top 78, a bottom 80 and a connector PCB 82. The PCB 82 includes connecting elements 84, which are arranged and configured to engage electrically and electronically to a unit, to which in use the connector will be connected. The skilled person will understand that the specific format of the connecting elements 84 may be selected so as to enable interface to a desired other unit. In one example a dedicated designed connector is provided whereas in one example one or more USB formats could be used as the connecting elements 84.

The top and bottom 78 and 80, are preferably made up of a plastic material such as ABS—Acrylonitrile Butadiene Styrene, and manufactured using plastic injection methods. The connector electronic PCB 82 has an important role as it serves as an authentication unit in the swallow sensor probe assembly and provides a connection between a monitor such as a dedicated bespoke monitor for use with the system, or a conventional computer screen or monitor, and the probe sensor.

As can be understood from for example, FIGS. 20 to 23, the connector enclosure is composed of two mechanical parts 78 and 80 arranged and sized and configured to mate with each other. These two pieces are tightly fit, i.e. press fit, into each other during the assembly so as to enclose and sandwich the electronic circuit board 82 securely within the housing. In one example some fixing mechanism such as a screw or rivet is applied once the top and bottom housing sections have been brought together, but preferably due to the materials used and the press fit mechanism no such fixing mechanism is required.

Figures 20, 21, 22, 23:
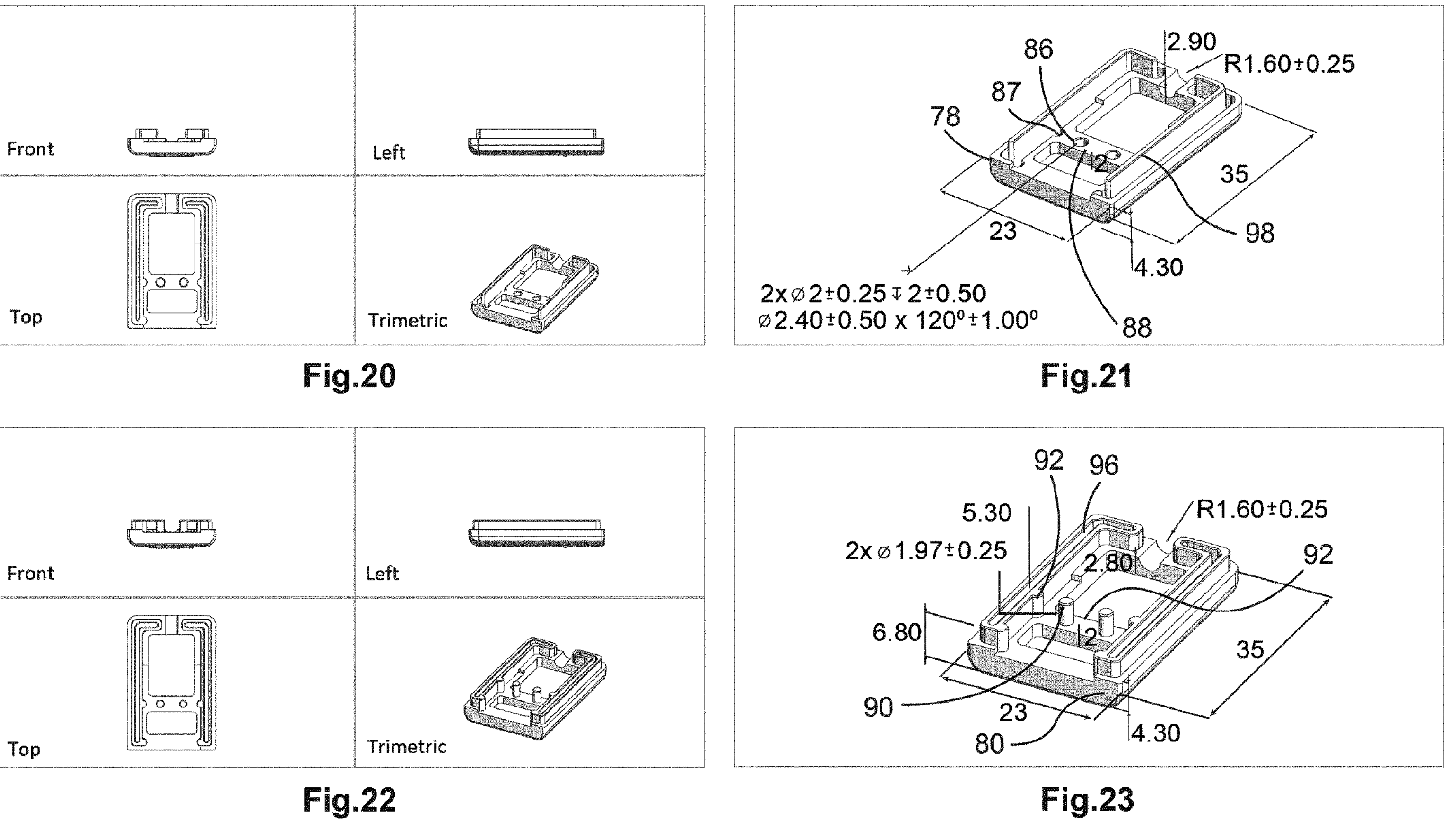
FIGS. 20 and 21 show views of the 3D Sketches for the connector enclosure top part.
FIGS. 22 and 23 show views of the 3D Sketches for the connector enclosure bottom part.

Referring to, say FIGS. 21 and 23, it can be seen that registration means is provided in each part of the housing. In the top 78, two female engagement members 86 are provided on a raised ridge 88 within the housing. On the corresponding part 80, two male engagement members 90, on a corresponding ridge 92, are sized and positioned so as to enable, upon engagement of the top and bottom housings, a press fit mating engagement with the female members 86. The significance of the position of members 86 and 90 is that they interact with the PCB 82, and in particular PCB side cut outs 94 to ensure alignment of the PCB within the housing when assembled. The raised ridges are raised so as to leave sufficient clearance to enable the PCB to be free of contact or juts contacted but without undue pressure when the housing is assembled.

Longitudinal recesses 96 are sized and arranged to engage with longitudinal projections 98 on the other part of the housing again to ensure many points of connection for the press fit engagement when the connector is assembled. By providing multiple points, preferably at least 3, for a press fit connection, the need for any additional connecting or fixing means is obviated whilst still ensuring that assembly can be done quickly and reliably. In this example of FIGS. 21 and 23 there are at least 6, including 2 central posts 86, two side posts 87 (half encompassed within the side members), and then 2 longitudinal recesses 96 and projections 98. It will be appreciated that generally for each of the top and bottom parts of the connector housing, as in this specific non-limiting example, it is preferred that both male and female parts for press fit are provided in each piece (top and bottom) of the housing with corresponding parts on the other piece of the housing.

Figures 24, 25:
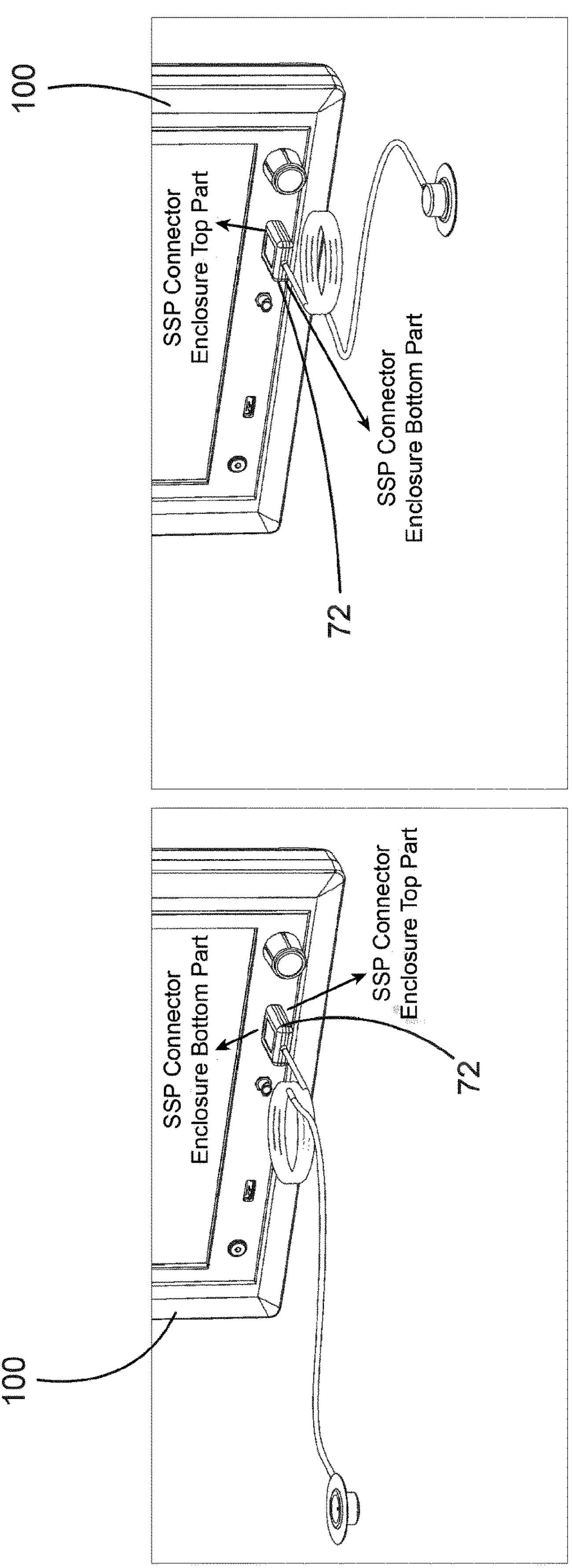
FIGS. 24 and 25 show schematic views of the connector connected to a monitor screen or unit.

FIGS. 24 and 25 show schematic views of the connector connected to a monitor screen or unit. As can be seen, the connector 72 is plugged into a corresponding socket provided on a unit such as a monitor of a PC 100 or a dedicated processing system for use with the swallow sensor probe. The connectors on the probe are preferably symmetrical about a horizontal plane (with respect to the orientation shown in FIG. 19), such that the connector 72 can be plugged in either way up. A shown in FIGS. 24 and 25, the connector can be plugged in in either orientation without affecting performance. This is achieved by the arrangement of the electrical connectors 84 on the connector PCB. Preferably the symmetry of the electrical connectors 84 is about a longitudinal vertical plane too.

Figure 26:
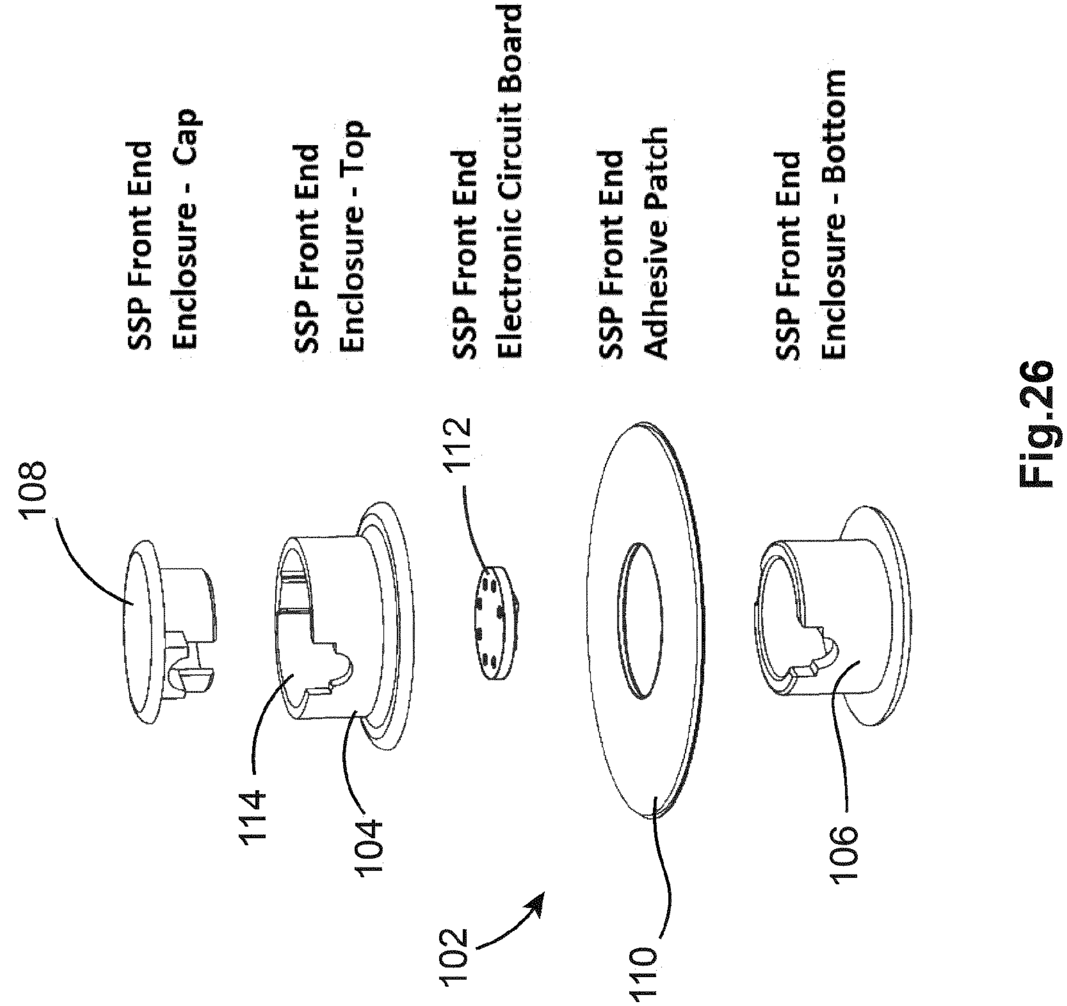
FIG. 26 is an exploded view of the internal structure of the swallow sensor probe front end assembly.

FIG. 26 is an exploded view of the internal structure of the swallow sensor probe front end assembly 102, shown in unexploded form in FIG. 18B as component 74.

The SSP front end assembly 102 is the part of the swallow sensor probe that is in contact with the subject. As mentioned earlier, the swallow sensor probe (SSP) employs a digital microphone sensor in order to acquire acoustic signals from a subject which are then processed by the system as described above. Similar to the connector described above with reference to FIGS. 19 to 25, the SSP front end assembly is composed of mechanical enclosure parts and an electronic circuit board. Beside these, an adhesive patch is used for attaching the SSP front-end assembly to a subject under test. The construction of the assembly is shown in FIG. 26.

The assembly is composed of 3 pieces of plastic enclosures, an adhesive patch and an electronic circuit board occupying the digital microphone sensor.

The SSP front-end electronic circuit board is enclosed by a mechanical design composed of 3 parts. These parts are introduced in FIG. 26 and referred to herein as the front-end enclosure top 104, the front-end enclosure bottom 106 and the front-end enclosure cap 108. The arrangement and configuration of these parts will now be described below.

The enclosure parts are designed in such a way that minimal effort is required in the assembly of the SSP front-end assembly. The front-end enclosure bottom 106 and front-end enclosure top 104 parts form the base of the assembly 102, such that they sandwich the adhesive patch 110 in between. The front-end electronic circuit board 112 assembled with the cable is mounted inside this base and, finally during assembly, the front-end enclosure cap 108 is press fit into the opening 114 of the top 104.

Figure 28:
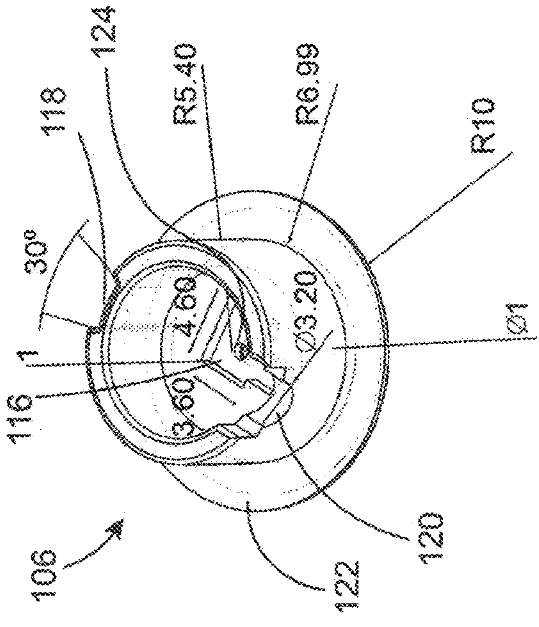
FIGS. 27 and 28 are views of the front-end assembly enclosure bottom part.
Figure 27:
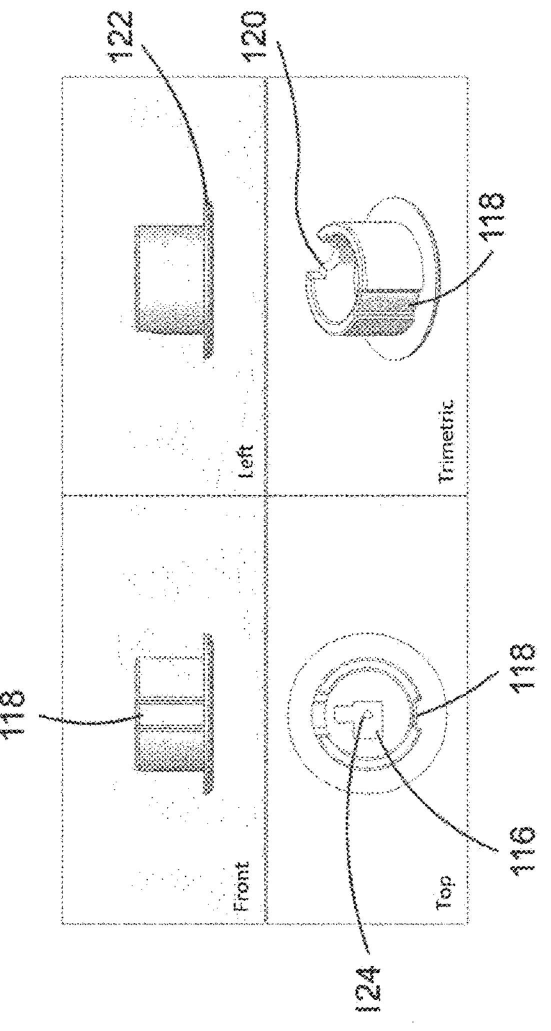

Referring now in sequence to each of the parts, FIGS. 27 and 28 show various views of the bottom 106. There is provided a recessed region 116 (seen most clearly in the top view) that serves as a bed for a digital microphone sensor provided when assembled inside the enclosure part. A recessed longitudinal groove 118 is provided which acts as an alignment means for ensuring precise alignment of other parts of the assembly when they are brought together and assembled. A cable notch 120 is provided which provides a route for the connecting cable to enter the central region of the assembly and to connect to a PCB and microphone when assembled. A can be seen the part 106 has a general format of a top hat with a rim 122 that in use engages with other parts of the assembled SSP front end, as will be described below. A hole 124 is provided in the base which provides a line of sight (or sound) connection for transmission and reception of sound from a subject to the microphone enclosed with thin the SSP front end assembly.

Figures 29, 30:
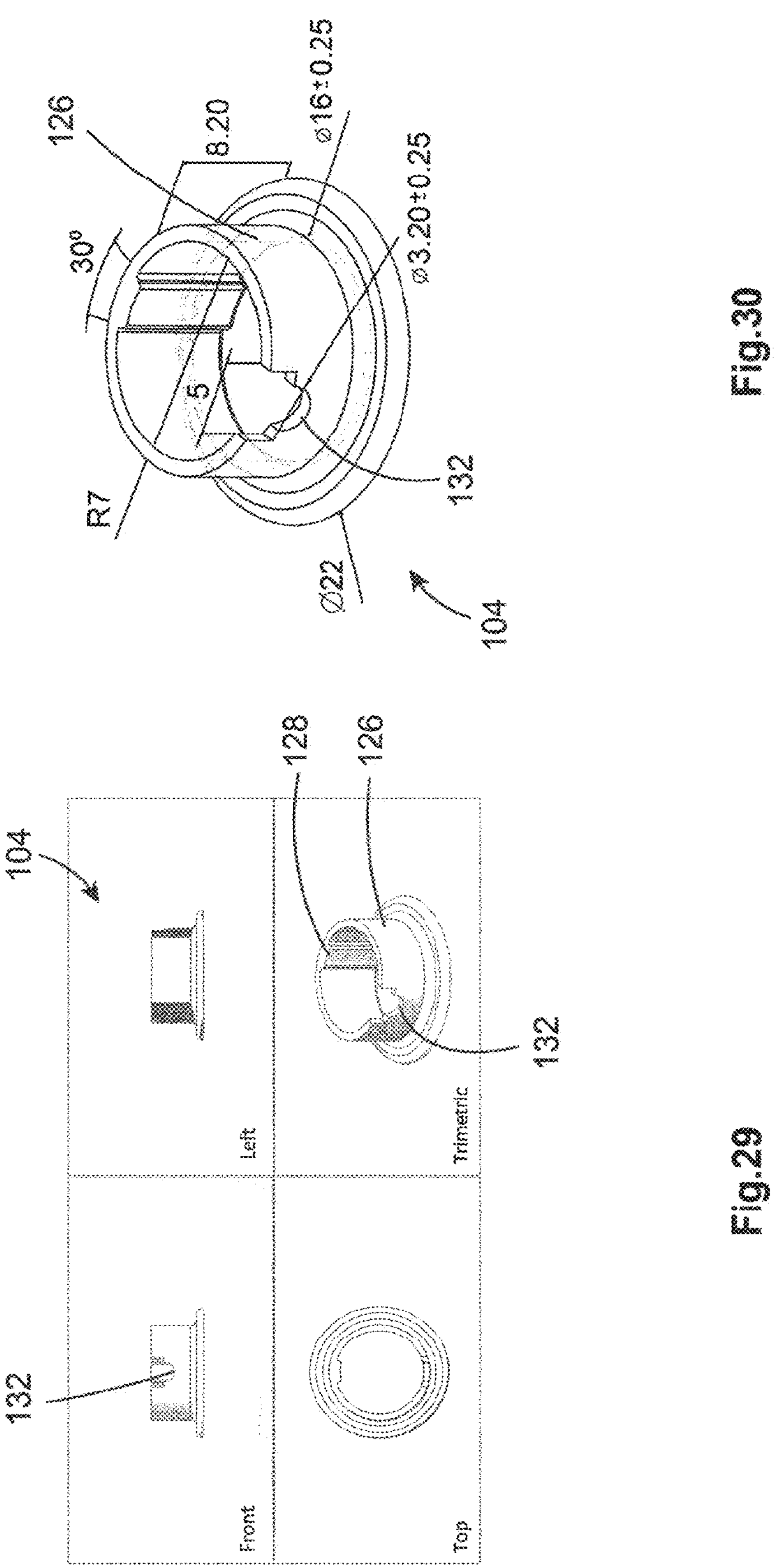
FIGS. 29 and 30 are views of the front-end enclosure top part.

FIGS. 29 and 30 are views of the front-end enclosure top part 104. As can be seen it is sized and configured to fit on top of the bottom part 106. It is provided with a generally cylindrical housing 126 having an inner diameter that is about the same as the outer diameter of the cylindrical housing of the bottom part 106 described above. A longitudinal key 128 is formed on the inner cylindrical wall which upon assembly engages with the slot 118 of the bottom part 106. Thus, longitudinal alignment between the two parts is ensured.

In addition, a cable notch 132 is provided such that when assembled with the bottom part 106, there exists a notch formed from both the top and bottom parts to provide access for a cable to the shared central region of the two parts. As can be seen the top part 104 also has a generally open top hat configuration. To assemble, initially the bottom part 106 is positioned on a clean assembly surface. Then an adhesive patch, which is typically ring or donut shape is arranged around it. Then the top part is press fit on top of the bottom part, effectively sandwiching the adhesive front patch between the rim of the top hats of the bottom 106 and top 104 parts. Then, once any required electronic circuity or components such as PCB 112 have been positioned within the SSP and connections with any wires have been established or fixed, the cap 108 can be inserted to close it.

Figures 31, 32:
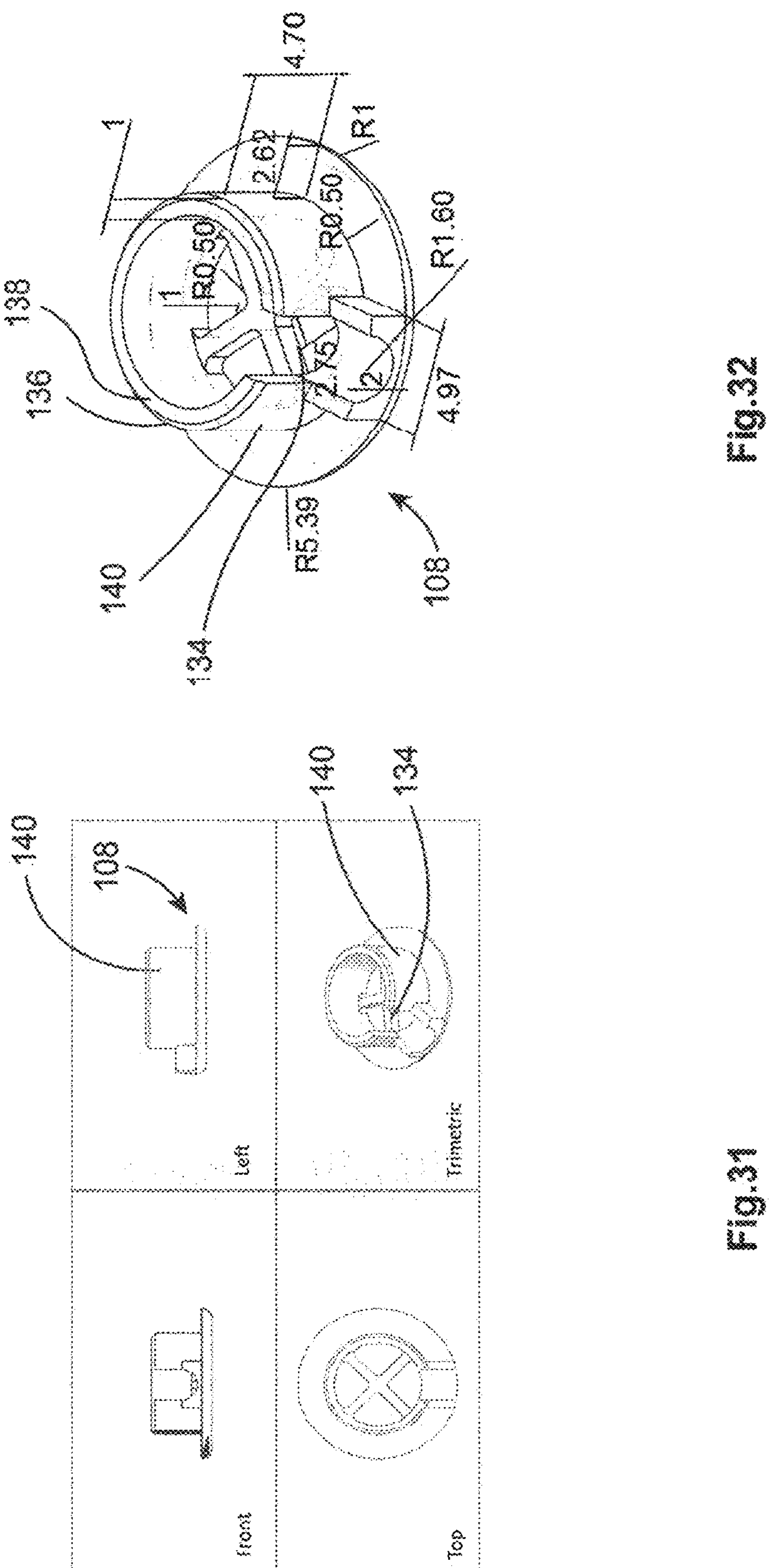
FIGS. 31 and 32 are views of the front-end enclosure cap part.

FIGS. 31 and 32 are views of the front-end enclosure cap part. The cap 108 is sized to press fit into the cylindrical opening of the top part of the SSP. It has a simple top hat form with an outer diameter selected to fit tightly into the inner diameter of the opening 114 of the top part 104. A generally cruciform strengthening structure is provided on the underside of the upper surface of the top, which provides strength and rigidity to the cap but also serves to ensure compression of the components within the SSP so as to ensure that they do not become damaged due being dislodged or knocked in use.

A cable notch 134 is provided again to correspond to the cable notches provided in both the bottom and top parts to provide a route for a connecting into the central region with the SSP.

An upper chamfered edge 136 is provided on the ring-shape end surface 138 of the circumferential wall 140 of the cap 108.

Figure 33:
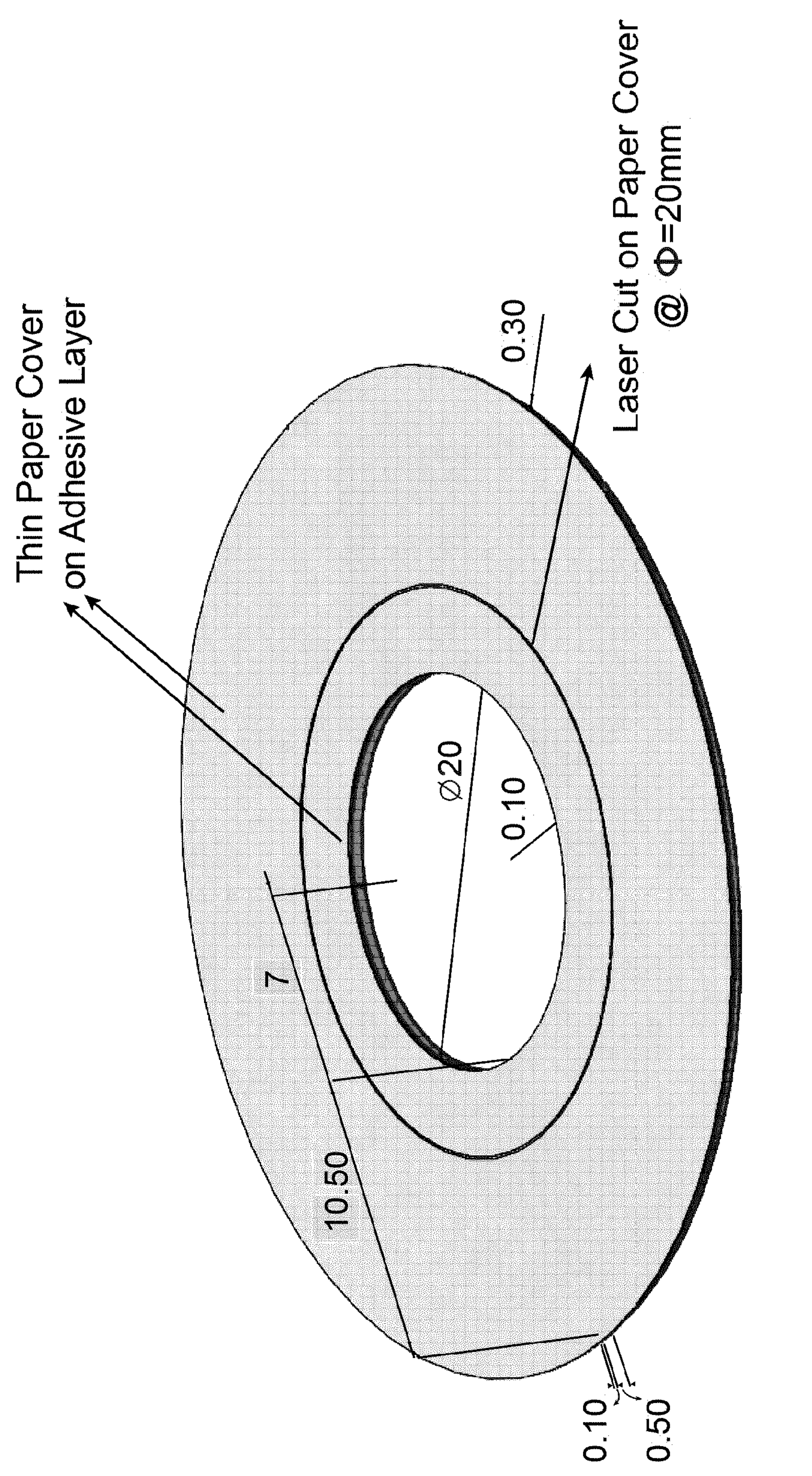
FIG. 33 is a bottom view of the adhesive patch for use in the sensor probe.

FIG. 33 is a bottom view of the adhesive patch for use in the sensor probe. The adhesive patch is a part of the SSP front-end assembly which is used to attach the probe assembly to a subject, in use. It is made up of a physical crosslinked polyolefin foam and an adhesive layer of acrylate copolymer covered by a thin protective paper. The patch may preferably be processed to be a desired shape using laser cutting or any other appropriate form of manufacture.

The geometry of the adhesive patch is shown schematically in FIG. 33. In this non-limiting example, the patch is made up of 0.5 mm thick biocompatible foam structured in a circular disk shape with an outer diameter of 35 mm. A thin biocompatible adhesive layer of acrylate copolymer is provided on the bottom layer which is covered by a thin paper film. An inner paper cover disk is removed during the assembly of the SSP front-end. The outer paper cover disk is removed just before the probe use so as to expose the adhesive for engagement with the skin of a subject.

Figure 34:
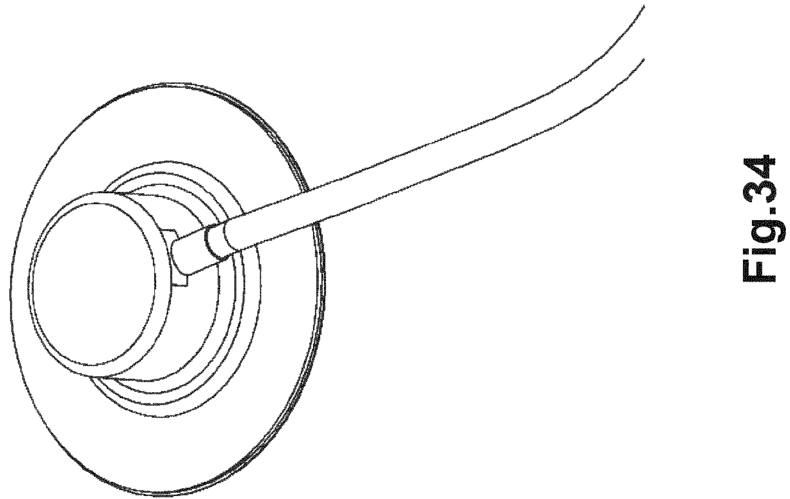
FIG. 34 is a view of the finalised assembly front end part.

FIG. 34 is a view of the finalised assembly front end part. Assembly may be achieved in a simple and reliable manner. By way of example a simple process for assembly will now be described.

Initially, the connector board of the SSP electronics assembly is used to interface with the connector enclosure. The enclosure parts (SSP connector enclosure parts and SSP front end enclosure parts) are prepared on an assembly table. The SSP connector enclosure bottom part 80 is interfaced with the SSP connector electronics board 82. The board 82 is mounted into the enclosure such that the two columns 90 of the enclosure bottom part go through the two holes of the board and the top layer of the board firmly contacts with the surface inside enclosure. The middle two columns 90 of the enclosure are preferably inserted into holes formed all the way through the PCB board 82.

After that, the connector enclosure top part is closed on top of the bottom part. The connector enclosure top part 78 is firmly inserted on top of the connector enclosure bottom part, squeezing the SSP connector electronic circuit board in between the two mechanical parts 78 and 80.

In the final step of the SSP assembly process, the front end electronic circuit board 112 is encapsulated inside the SSP 102.

The front end enclosure bottom part 106 and the adhesive patch 110 will be interfaced. To do this, an inner protective paper cover of the adhesive patch is removed exposing a sticky ring region and the front end enclosure bottom part 106 is inserted through middle of the adhesive patch 110.

The SSP front end enclosure bottom part 106 is placed inside the adhesive patch 110 from the bottom such that the inner region of the patch where the protective paper cover is removed is adhered to the front end enclosure bottom part.

The next step is the introduction of the front end enclosure top part 104 to this assembly. The front end enclosure top part 104 is placed upon the enclosure bottom part 106. The part is inserted from the top of the front end enclosure bottom part orienting the cable entrance surfaces of both parts.

The bottom part 106 of the enclosure is passed through the top part compressing the adhesive patch 110 in between. Now, the SSP front end electronics board 112, (preferably tied to the SSP cable and the connector assembly) can be placed inside this mechanical assembly. The front end electronics PCB 112 is placed inside the enclosure assembly from the top, orienting the SSP cable with the half circle hole 120 and 132 on the front.

Note that there is a recess as mentioned above 116 inside the enclosure bottom part 106 that is sized to receive and fit a microphone sensor and capacitors or any other electronics on the front end PCB 112. The orientation of these parts and the enclosure bottom part is preferably matched.

Finally, the enclosure cap 108 is mounted on top of the front end enclosure assembly concealing the SSP front end PCB board. The cap should be inserted into the enclosure assembly orienting the faces for cable entrance. Small pressure is required to compress the SSP front-end PCB between the cap and the enclosure base. Closing the enclosure cap on top of the enclosure base conceals the SSP front-end PCB inside. A small amount of pressure is applied on top of the cap for close fit. Doing so pushes the SSP front-end PCB and the microphone sensor up to the sensor gap surface on the enclosure bottom part.

Embodiments of the present description have been described with particular reference to the examples illustrated. However, it will be appreciated that variations and modifications may be made to the examples described within the scope of the present description.

The invention claimed is:

1. A method for monitoring feeding maturation in a premature baby, the method comprising:

measuring an acoustic response from a baby during a selected time period to provide energy constrained spectral content information;

comparing the measured acoustic response against a train data set to determine an indication of a swallow event;

measuring a respiration pattern of the baby during a swallow cycle using a peak and valley model to provide respiration data; and determining a feeding maturity of the baby in dependence on the swallow indication and respiration data, wherein measuring the acoustic response from the baby during the selected time period comprises extracting features from a received signal and comparing the extracted features against the train data set, wherein the extracted features may be classified as swallow or non-swallow events, and wherein, prior to extracting features, a received signal is framed so as to be considered as stationary.

2. The method of claim 1, wherein the comparison against the train data set comprises comparing extracted features in a classification process.

3. The method of claim 2, wherein the extracted features are determined based on feature extraction performed using a speech analysis tool.

4. The method of claim 3, wherein the feature extraction comprises labelling identified features as one or more of features selected from a group including:

a swallow sound;

a final discrete sound;

a respiration sound; and other non-swallow sounds including a vowel sound, a pleasure sound, or a crying sound.

5. The method of claim 1, further comprising determining the feeding maturity based on maximum rhythmic swallow numbers and an average time between swallows.

6. The method of claim 1, wherein training of the train data set comprises:

receiving audio samples from healthy subjects;

framing the received audio samples so as to provide stationary signals; and extracting features from the framed samples so as to generate the train data set.

7. The method of claim 1, wherein the peak and valley model to determine respiration data comprises:

receiving an input signal indicating respiration of the baby;

processing the received input signal with a low pass filter so as to provide a smoothed respiration signal; and extracting parameters associated with the respiration based on the smoothed respiration signal.

8. The method of claim 7, wherein the parameters include one or more of a breath rate, and an onset or end of an inspiration or expiration event.

9. The method of claim 1, further comprising:

determining an inspiration after swallow count in dependence on the swallow indication and respiration data, wherein the inspiration after swallow count indicates a number of inspiration events occurring just after a swallow event has finished; and determining that the feeding maturity of the baby has decreased based on the inspiration after swallow count increasing.

10. A device for monitoring feeding maturation in a premature baby, the device comprising:

a first sensor configured to measure an acoustic response from a baby during a selected time period to provide energy constrained spectral content information;

a second sensor configured to measure a respiration pattern of the baby during a swallow cycle;

a processor coupled to the first and second sensors, the processor configured to:

compare the measured acoustic response against a train data set to determine an indication of a swallow event; and provide respiration data based on the measured respiration pattern and using a peak and valley model; and determining a feeding maturity of the baby in dependence on the swallow indication and respiration data, wherein measuring the acoustic response from the baby during the selected time period comprises extracting features from a received signal and comparing the extracted features against the train data set, wherein the extracted features may be classified as swallow or non-swallow events, and wherein, prior to extracting features, a received signal is framed so as to be considered as stationary.

11. The device of claim 10, wherein the processor is configured to train the data set by:

receiving audio samples from healthy subjects;

framing the received audio samples so as to provide stationary signals; and extracting features from the framed samples so as to generate the train data set.

12. The device of claim 10, wherein the processor is configured to apply the peak and valley model to determine respiration data by:

receiving an input signal indicating respiration of the baby;

processing the received input signal with a low pass filter so as to provide a smoothed respiration signal; and extracting parameters associated with the respiration based on the smoothed respiration signal.

* * * * *